US006172205B1

(12) United States Patent
Danishefsky et al.

(10) Patent No.: US 6,172,205 B1
(45) Date of Patent: Jan. 9, 2001

(54) SYNTHETIC PROCESS TOWARD TOTAL SYNTHESIS OF ELEUTHEROBIN AND ITS ANALOGUES AND USES THEREOF

(75) Inventors: Samuel J. Danishefsky, Englewood, NJ (US); Xiao-Tao Chen, New York, NY (US); Clare E. Gutteridge, New York, NY (US); Samit K. Bhattacharya, New York, NY (US); Bishan Zhou, New York, NY (US)

(73) Assignee: The Trustees of Columbia in the City of New York, New York, NY (US)

( * ) Notice: Under 35 U.S.C. 154(b), the term of this patent shall be extended for 0 days.

(21) Appl. No.: 09/210,290

(22) Filed: Dec. 11, 1998

Related U.S. Application Data

(60) Provisional application No. 60/069,248, filed on Dec. 11, 1997.

(51) Int. Cl.[7] .................................................. C07G 11/00
(52) U.S. Cl. .............................. 536/4.1; 514/25; 514/32; 536/17.3; 536/18.1; 548/300.1; 548/311.1; 548/311.4
(58) Field of Search .................. 514/25, 32; 536/4.1, 536/17.3, 18.1; 548/300.1, 311.1, 311.4

(56) References Cited

U.S. PATENT DOCUMENTS

| | | | |
|---|---|---|---|
| 5,473,057 | * 12/1995 | Fenical et al. | 536/17.3 |
| 5,869,514 | * 2/1999 | Battistini et al. | 514/397 |
| 5,922,750 | * 7/1999 | Battistini et al. | 514/397 |

FOREIGN PATENT DOCUMENTS

99/21862 * 5/1999 (WO) .
99/29704 * 6/1999 (WO) .

OTHER PUBLICATIONS

Lindel, et al. (1997) "Eleutherobin, a New Cytotoxin that Mimics Paclitaxel (Taxol) by Stabilizing Microtubules", *J. of the Am. Chem. Soc.*, 119(37):8744–8745.
Nicolaou and Sorensen. Classics in Total Synthesis (Chapter 1), published by VCH, pp. 1–19, 1996.*
Ketzinel et al. "Sarcodictyin A and Two Novel Diterpenoid Glycosides, Eleuthosides A and B, from the Soft Coral *Eleutherobia aurea*", J. Natl. Prod., vol. 59, pp. 873–875, 1996.*
Chen, X., et al., (1998) "A Convergent Route for the Total Synthesis of the Eleuthesides", *Angew. Chem. Int. Ed.*, 37(1/2):185–187 (Exhibit 1).
Chen, X., et al., (1998) "The Total Synthesis of eleutherobin: A Surprise Ending", *Angew. Chem. Int. Ed.*, 37(6):789–792 (Exhibit 2).

(List continued on next page.)

*Primary Examiner*—Howard C. Lee
(74) *Attorney, Agent, or Firm*—John P. White; Cooper & Dunham LLP

(57) ABSTRACT

This invention provides a process for the preparation of a Eleutherobin derivative of the formula:

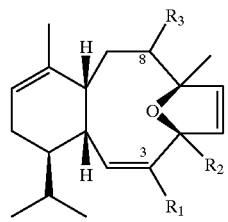

wherein $R_1$ is a hydrogen, ester, nitrile or $C_2H_4$—R wherein $R_4$ is a carbohydrate, an alcohol an amine, an amide, an alkyne, or, $R_2$ is a linear or branched alkyl moiety, $R_3$ is an ester, an amide, a carbamate, an acetal compound, an ether or a urethane, $R_4$ is a hydrogen or $CH_2$, position $C_2$ and $C_3$ is cis or trans, position $C_8$ is α or β and a compound is produced having the structures:

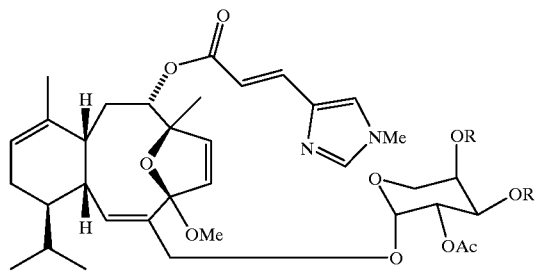

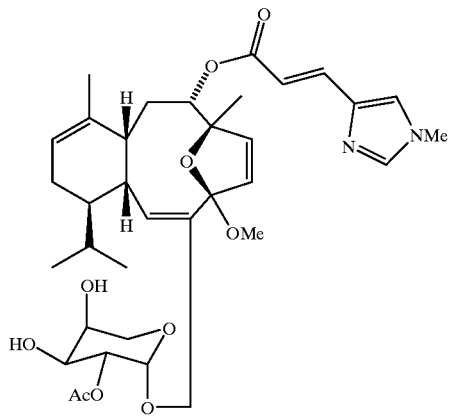

Additionally, this experiment provides a method for inhibiting growth of cancerous cells comprising contracting an amount of Eleutherobin derivative effective to inhibit the growth of said cells. Further provided is a method for treating cancer in a subject which comprises administering to the subject a therapeutically effective amount of the Eleutherobin derivative.

10 Claims, 12 Drawing Sheets

OTHER PUBLICATIONS

Cintas, P., (1991) "Addition of Organochromium Compounds to Aldehydes: The Nozaki–Hiyama Reaction", Dept. Of. Org. Chem., 249–257 (Exhibit 3).

Eckhardt, M., et al., (1996) "The First Syntheses of 6–/10–membered Ring Analogs and of a 6–11/–Membered Ring Analog of the Dienediyne Core of the Neocarzinostatin Chromophore by Ring–Closure According to the Nozaki–Hiyama Reaction", *Liebigs Ann.*, 473–488 (Exhibit 4).

Garegg, P.J., et al., (1983) "A reinvestigation of glycosidation reactions using 1–thioglycosides as glycosyl donors and thiophilic cations as promoters", *Carb. Res.*, 115:162–165 (Exhibit 5).

Greenlee, M., (1981) "Total Synthesis of (±)–Trihydroxydecipiadiene", *J. Am. Chem. Soc.*, 103:2425–2326 (Exhibit 6).

Hung, D.T., et al., (1996) "(+)–Discodermolide binds to microtubules in stoichiometric ration to tubulin dimers, blocks taxol binding and results in mitotic arrest", *Chem. & Biol.*, 3(4):287–293 (Exhibit 7).

Hung, D.T., et al., (1996) "Understanding and controlling the cell cycle with natural products", *Chem. & Bio.*, 3(8):623–639 (Exhibit 8).

Kanazawa, A., et al., (1997) "Convergent, enantioselective synthesis of the novel furanoditerpene (+)–taoianone through facially selective chiral olefin–keten [2+2] cycloaddition", *J. Chem. Soc.*, 1911–1912 (Exhibit 9).

Long, B.H., et al., (1998) "Eleutherobin, a Novel Cytotoxic Agent That Induces Tublin Polymerization, Is Similar to Paclitaxel (Txol)", *Can. Res.*, 58:1111–1115 (Exhibit 10).

Lonn, H., (1985) "Synthesis of a Tri–and A Hepta–Saccharide4 which contain $_{a\textit{f}}$–Fucopyranosyl groups and are part of the complex type of carbohydrate moiety of glycoproteins", *Els. Sci.*, 139:105–113 (Exhibit 11).

Nicolaou, et al., (1998) "Solid and Solution Phase Synthesis and Biological Evaluation of Combinatorial Sarcodictyin Libraries", *J. Am. Chem. Soc.*, 120:10814–10826 (Exhibit 12).

Nicolaou, et al., (1998) "Synthesis and Biological Activity of Sarcodictyins", *Angew. Chem. Int. Ed.*, 37(10):1418–1421 (Exhibit 13).

Nicolaou, et al., (1997) "Synthesis of the Tricyclic Core of Eleutherobin and Sarcodictyins and Total Synthesis of Sarcodictyin A", *J. Am. Chem. Soc.*, 119:11353–11354 (Exhibit 14).

Nicolaou, et al., (1997) "Total Synthesis of Eleutherobin", *Angew. Chem. Int. Ed. Engl.*, 36(22): 2520–2524 (Exhibit 15).

Rao, S., et al., "3'–(p–Azidobezamido) taxol Photolabels the N–terminal 31 Amino Acids of $\beta$–Tubulin", *J. Biol. Chem.*, 269(5):3132–3134 (Exhibit 16).

Scott, E.W., et al., (1986) "Palladium–CAtalyzed Coupling of Vinyl Triflates with Organostannanes Synthetic and Mechanistic Studies", *J. Am. Chem. Soc.*, 108(11):3033–3040 (Exhibit 17).

Trost, B.M., et al., (1974) "New Synthetic Reactions. Geminal Alkylation via $\alpha$–Trimethylenedithiocyclobutanones[1]", *J. Am. Chem. Soc.*, 97(8):2224–2232 (Exhibit 18).

\* cited by examiner

1: eleutherobin

2: sarcodictyin

3: valdivone A

FIGURE 6C

| | $R_1$ | $R_2$ |
|---|---|---|
| Neo-Eleutherobin | $CH_2$-L-β-2'-O-acetylarabinose glycoside | $N(1)$-methylurocanic acid ester |
| SKBII.294 | $CH_2OAc$ | $N(1)$-methylurocanic acid ester |
| SKBII.296 | H | $N(1)$-methylurocanic acid ester |
| SKBII.298 | $CH_2OH$ | $N(1)$-methylurocanic acid ester |
| SKBIII.13 | $CH_2$-D-β-arabinose glycoside | OH | a) MeOTf, DTBP, CH$_2$Cl$_2$/Et$_2$O (1:2), molecular sieves (4 Å), 0°C, 93% ($\alpha$:$\beta$ = 1:1); b) TBAF, THF, 20°C, ≈98%; Ac$_2$O, DMAP, CH$_2$Cl$_2$, 20°C, ≈99%. DMAP = 4-dimethylaminopyridine; DTBP = 2,6-di-tert-butylpyridine; TBAF = tetrabutylammonium fluoride.

a) Pd(PPh$_3$)$_4$, LiCl, 2-amino-5-chloropyridine, THF, Δ, ≈40-50%: b) TBAF, THF, 20°C, 67%; c) DCC, DMAP, PhCH$_3$, 50°C, ≈80%; d) PPTS, MeOH, Δ, ≈70%.
DCC = dicyclohexylcarbodiimide, DMAP = 4-dimethylaminopyridine; PPTS = pyridinium p-toluenesulfonate; TBAF = tetrabutylammonium fluoride.

SYNTHETIC PROCESS TOWARD TOTAL SYNTHESIS OF ELEUTHEROBIN AND ITS ANALOGUES AND USES THEREOF

This application claims the benefit of U.S. Provisional Application No. 60/069,248, filed Dec. 11, 1997, the content of which is hereby incorporated into this application by reference.

The invention disclosed herein was made with Government support under NIH Grant No. HL 25848 from the Department of Health and Human Services. Accordingly, the U.S. Government has certain rights in this invention.

BACKGROUND OF THE INVENTION

Throughout this application, various references are referred to within parentheses. Disclosures of these publications in their entireties are hereby incorporated by reference into this application to more fully describe the state of the art to which this invention pertains.

The marine environment is taking its place beside plant sources and fermentation in providing access to biologically active substances (30). From the standpoint of organic chemistry, this aquatic biomass warrants particularly close attention, due to the richly varied structures provided therein. Moreover, the reliability of marine feedstocks as a bulk source of natural products is often less than the case with their plant and microbially derived counter parts. Hence, marine derived natural products may well furnish excellent opportunities for the subspecialty of synthesis.

Such an opportunity is presented by a group of structurally related natural products which is loosely group under the term "eleuthesides" (cf. inter alia eleutherobin (31), sarcodictyn (32) and valdivone (33).

These are each isolated from different marine sources. Interest in the family was considerably heightened by the recent report that eleutherobin displays excellent potency in a variety of tumor cell lines and that the mechanism of its cytotoxicity promotes the polymerization of stable microtubules (31). Thus, at least eleutherobin, manifests a taxol-epothilone-discodermolide mode of action (34). In light of the very interesting structures of these closely related compounds, the high potency of eleutherobin, and the difficult availablity of all of the eleuthesides from their natural habitats, this family presents a challenging opportunity for creative chemistry.

Eleutherobin, a natural product isolated from a marine soft coral, is an antimitotic agent that promotes the polymerization of stable microtubules. Although its mechanism of action is similar to that of Taxol, its structure is distinct. A structure-activity profile of five synthetic eleutherobin derivatives that have modifications at C3, C8 and C15 is reported. Cytotoxicity, the ability to polymerize stable microtubules and the induction of microtubule bundles in cells were assessed. Eleutherobin had an $IC_{50}$ value comparable at Taxol, whereas neo-eleutherobin, which carries a carbohydrate domain that is enantiomeric with that of the parental product, had 690 of the microtubule polymerization ability of eleutherobin and was 20-fold less cytotoxic. Both of these compounds exhibited cross-resistance in an MDR1 expressing cell line, Removal or replacement of the C15 sugar moiety resulted in reduced microtubule polymerization and cytotoxicity compared to eleutherobin and loss of cross-resistance at the ovarian carcinoma cell line SKVBL that expresses high levels of P-glycoprotein. Hence, removal of the sugar moiety alters the cytotoxic potency of eleutherobin and its cross-resistance pattern in Taxol-resistant cells, though such compounds retain the microtubule stabilizing activity of eleutherobin. By contrast, removal of the urocanic acid group at C8 resulted in virtually complete abrogation of biological activity. The compound lost is ability to polymerize microtubules, and its cytotoxicity was reduced by a minimum of 2000-fold in lung carcinoma A549 cells. Thus, our data indicate that the N(1)-methylurocanic acid moiety of eleutherobin or a structurally similar moiety is essential for Taxol-like activity. These findings will be important for the future design and synthesis of new and. more potent eleutherobin analogues.

Synthesis of the tricyclic core of eleutherobin and sarcodictyn has been reported by Nicolaou. (46) Additional work by Nicolaou includes a total synthesis of eleutherobin from the tricyclic core. (47, 48). This invention differs from the work of Nicolaou by providing a different synthetic process toward synthesis of the eleutherobin tricyclic core, eleutherobin and eleutherobin analogues.

The taxol-like activity of eleutherobin and sarcodictyins has been reported on by others. (48, 49) The mechanism of this activity was further investigated by Nicolaou. (50)

This invention provides a flexible and convergent synthesis of the eleuthesides providing significant quantities of end products, going beyond the completion of a ceremonial level route to the natural products.

SUMMARY OF THE INVENTION

The present invention provides a process for the preparation of a Eleutherobin derivative of the formula:

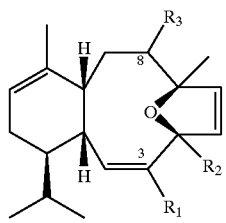

wherein
$R_1$ is a hydrogen, ester, nitrile, friflate or $CH_2-R_4$ wherein $R_4$ is a carbohydrate, an alcohol an amine, an amide, an alkyne,or $C_1-C_9$ linear or branched chain alkyl;
$R_2$ is a linear or branched alkyl moiety;
$R_3$ is an ester, an amide, a carbamate, an acetal compound, an ether or a urethane;
position $C_2$ and C is cis or trans;
position $C_8$ is α or β, comprising the steps of:
(a) treating a chiral matrix material with a ketene wherein, the chiral matrix material comprises R-(−)-α-phellandrene, under suitable conditions to form a compound having the structure:

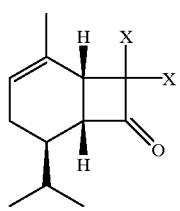

wherein X is a halogen; and
(b) Dehalogenating the compound in step (a) under suitable conditions to form a compound having the structure:

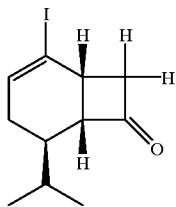

(c) subjecting the compound in step (b) to a Bredereck transformation to form a compound having the structure:

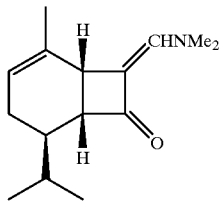

(d) acid catalyzing and fragmenting the compound in step(c) under suitable conditions to form a compound having the structure:

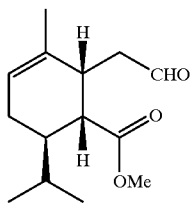

(e) appending a furanoid building block having the structure:

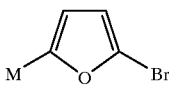

wherein M is selected from a group consisting of a metal, and the furanoid building block consists of 2,5-dibromofuran, to the compound formed in step (d) under suitable conditions to form a compound having the structure:

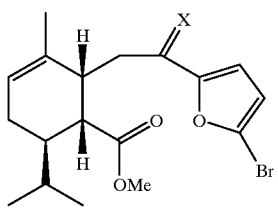

wherein X is α-OH, β-H or α-H, β-OH, α-OTBDPS, or β-OTBDPS (f) protecting the compound formed in step (e) under suitable conditions to form a compound having the structure:

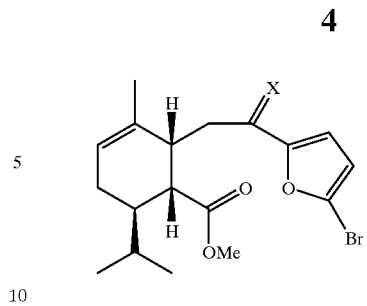

wherein X is α-OTBDPS, β-H or α-H, β-OTBDPS;

(g) expanding the compound in step (f) under suitable conditions to form a compound having the structure:

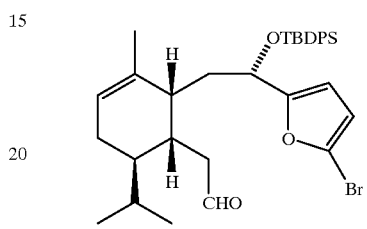

(h) performing a Nozaki-Kishi reaction on the compound in step (g) to form a compound having the structure:

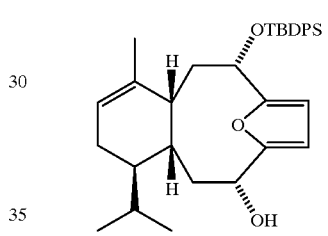

(i) protecting the compound formed in step (h) under suitable conditions to form a compound having the structure:

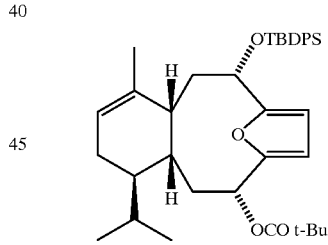

(j) treating the compound in step (i) under conditions suitable to the removal of OTBDPS to form a compound having the structure:

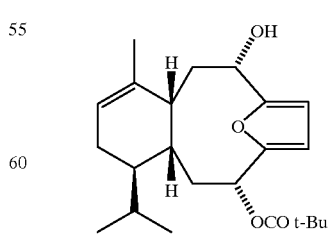

(k) treating the compound in step (j) with dimethyldioxirane under suitable conditions to form a compound having the structure:

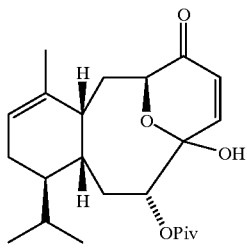

(l) protecting the compound in step (k) wherein, the protecting group consists of α-OTBDPS, β-H or α-H, β-OTBDPS, under suitable conditions to form a compound having the structure:

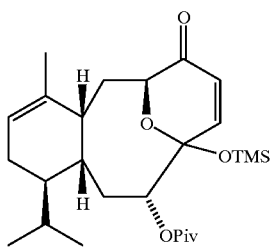

(m) methylating the compound in step (k) or (l) under suitable conditions to form a compound having the structure:

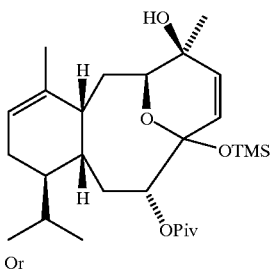

(1)

Or

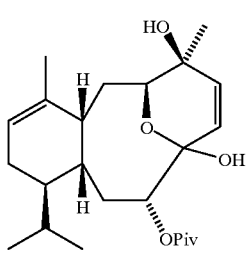

(2)

(n) treating compound (2) in step (m) with acetic anhydride under suitable conditions to form a compound having the structure:

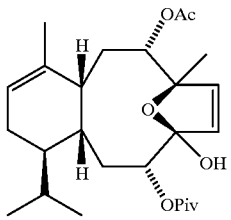

(o) acid catalyzing compound (1) in step (m) under suitable conditions to form a compound having the structure:

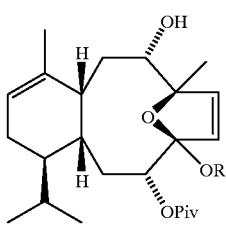

wherein

R is a linear or branched chain alkyl group.

(p) protecting, deprotecting and converting the compound in step (o) under suitable conditions to form a compound having the structure:

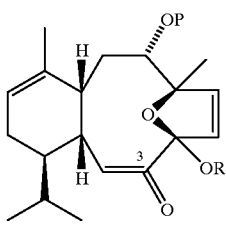

wherein

R is a linear or branched chain alkyl group and P is a protecting group.

(q) treating the compound in step (p) under suitable conditions to form a compound having the structure:

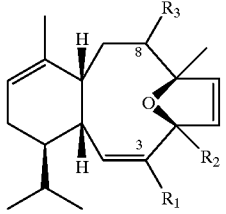

Wherein the compound in step (q) can be coupled to a carbohydrate, the carbohydrate consiting of D-arabinose, L-arabinose or D-galactose or a compound having the structure:

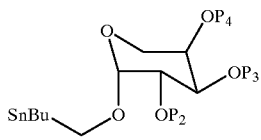

Wherein $P^2$, $P^3$, $P^4$, are Ac, H or other alkyl, acetyl groups; $P^2$ is H, SEM, or TBS when $P^3$ and $P^4$ are $C(Me)_2$; and the carbohydrate is synthesized by converting a compound:

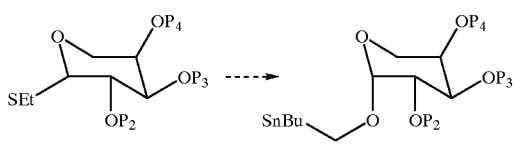

The present invention provides compound having the structure:

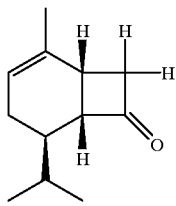

The present invention further provides a compound having the structure:

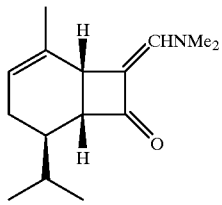

The present invention also provides a compound having the structure:

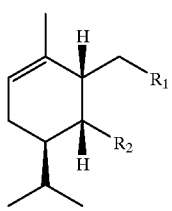

wherein $R_1$ and $R_2$ are an ester, acetal, nitrite or aldehyde.

The present invention provides a compound having the structure:

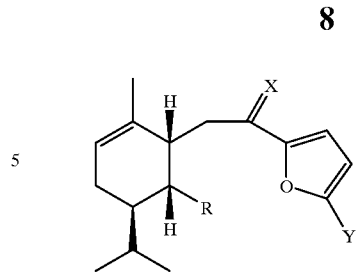

wherein

X is α-OH, β-H or α-H, β-OH;

$R_2$ is an ester, hydroxy methyl, nitrite, cyanomethyl;

Y is a halogen

This invention further provides a compound having the structure:

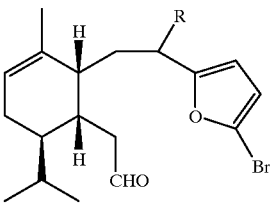

wherein the configuration of R is α or β and R is OTBDPS or a protecting group.

This invention also provides a compound having the structure:

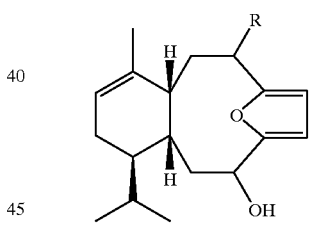

wherein the configuration of R is α or β and R is OTBDPS or a protecting group.

This invention also provides a compound having the structure:

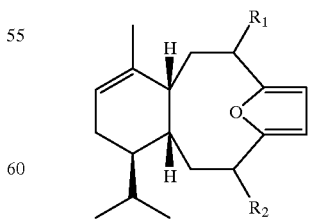

wherein the configuration of R is α or β and $R_1$ is OTBDPS or a protecting group and $R_2$ is OCOt—Bu or a protecting group.

This invention provides a compound having the structure:

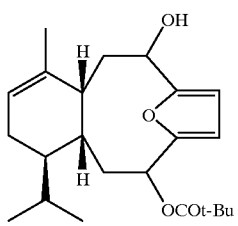

wherein the configuration OH is α or β.

This invention further provides a compound having the structure:

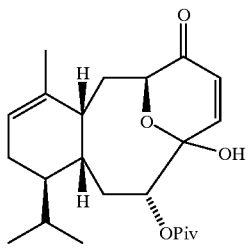

wherein the configuration is α or β.

This invention further provides a compound having the structure:

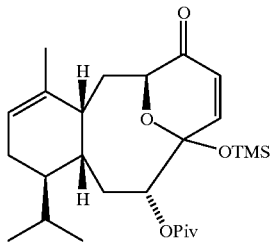

wherein the configuration is α or β.

This invention also provides a compound having the structure:

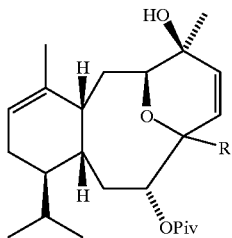

wherein R is OTMS, OH, or a protected hydroxyl group; and the compound is α or β.

This invention further provides a compound having the structure:

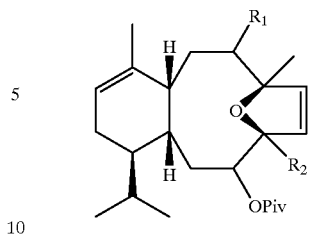

wherein $R_1$ is OAc or OH and$_2$ R is OH or a linear or branched alkyl protected hydroxyl group.

The present invention provides a compound having the structure:

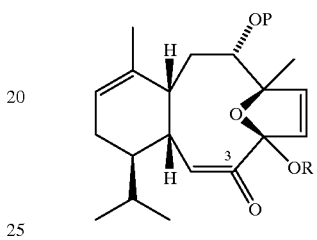

wherein P is a protecting group consisting of α-OTBDPS, β-H, α-H, β-OTBDPS and R isa linear or branched chain alkyl group.

The present invention provides a method for inhibiting growth of cancerous cells comprising contacting an amountof the compound to inhibit, reduce, or cause remission the cancer of a Eleutherobin analogue effective to inhibit the growth of said cells.

The present invention provides a method for treating cancer wherein, the cancer is a cancer of the breast, colon, lung, liver, brain or ovary. in a subject which comprises administering to the subject wherein, the administration comprising epidural, intraperitoneal, intramuscular, subcutaneous or intravenous injection; infusion; or topical, nasal, oral, anal, ocular or otic delivery, a therapeutically effective amount comprising an amount of the compound to inhibit, reduce, or cause remission of the cancer wherein the amount is from about 0.02 to about 10 mg/kg body weight of an Eleutherobin analogue.

Figure 1A:
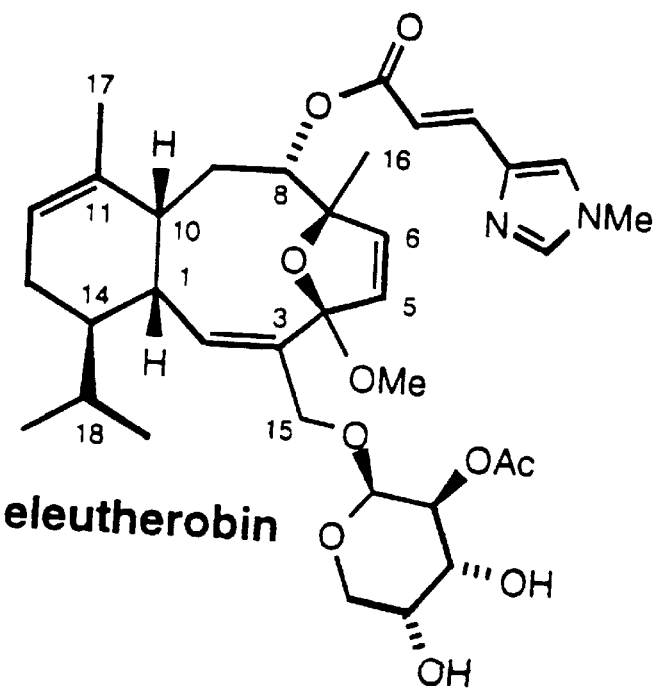
FIG. 1 illustrates the structures of naturally occuring eleuthesides.
Figure 1B:
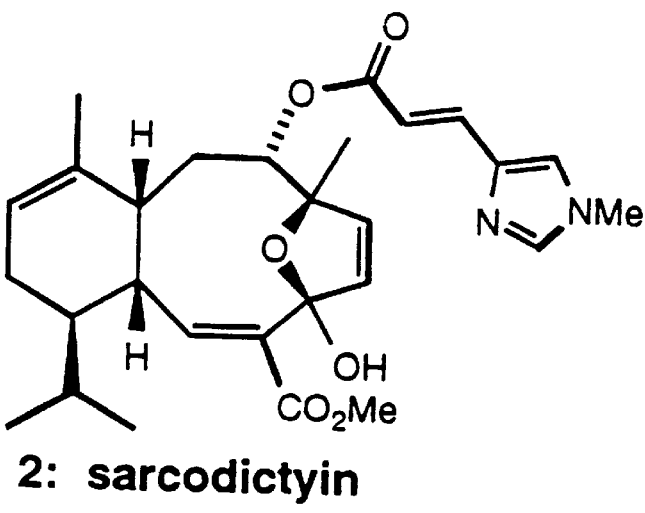
Figure 1C:
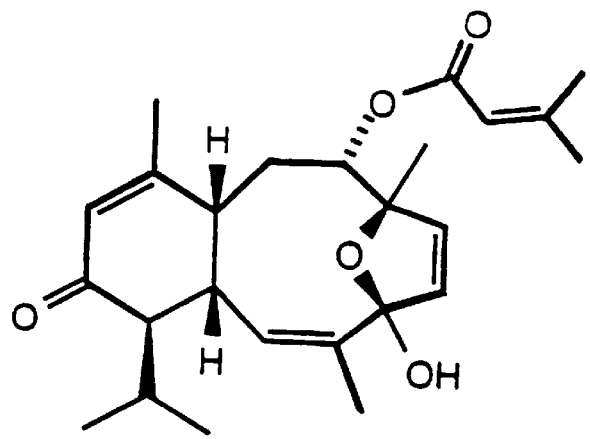

Illustrates the effects of eleutherobin and its derivatives on the morphology of cellular microtubules following exposure of cells to 2 μM of each compound for 5.5 h at 37° C. The extensive microtubule bundling observed in eleutherobin treated cells (Panel C), was identical to that seen in Taxol-treated cells (Panel B). Neo-eleutherobin treatment (Panel D) Also resulted in bundle formation. In this case however, the extent of bundling was reduced compared to panels B and C. Compounds SKBII.294 (Panel E), SKBII.296 and SKBII.298 (not shown) induced less bundle formation than neo-eleutherobin, and the quantity was significantly reduced when compared to either eleutherobin or Taxol. Cells exposed to SKBIII.13 (Panel F) displayed the same morphology, a fine microtubule network without bundle formation, as control cells treated with 0.1% DMSO only (Panel A). Multiple asters that are known to be present in mitotic cells treated with Taxol (23), were also seen in eleutherobin and neo-eleutherobin-treated cells (data not shown). The number of micotic asters correlated with the extent of microtubule bundling in interphase cells.

FIG. 10A synthesis of the (arabinosyl)methyl donors for Stille coupling. 10B synthesis of eleutherobin and neo-eleutherobin.

DETAILED DESCRIPTION OF THE INVENTION

As used herein, the term "linear or branched" alkyl moity encompasses, but is not limited to, methyl, ethyl, propyl, isopropyl, t-butyl, sec-butyl; cyclopentyl or cyclohexyl. The alkyl moity may contain one carbon atom or as many as fourteen carbon atoms, but preferably contains one carbon atom or as many as nine carbon atoms, and may be substituted by various groups, which include, but are not limited to, acyl, aryl, alkoxy, aryloxy, carboxy, hydroxy, carboxamido or N-acylamino moieties.

As used herein a "carbohydrate" encompasses, but is not limited to, monosaccharides, monosaccaride intramolecular hemiacetals, disaccharide, oligosaccharide or polysaccarides. Examples of carbohydrates include, but are not limited to ribose, arabinose, xylose, lyxose, allose, altrose, glucose, mannose, gulose, idose, galactose, talose, lactose, maltose, cellobiose, sucrose,N-Acetyl-D-glucosamine, D Glucuronic acid, L-Iduronic acid, N-Acetyl-D-Galactosamine, N-Acetylneuraminic acid, N-Acetylmuramic acid and $CH_2$-L-β-2"-O-acetylarabinose glycoside.

As used herein the term "ester" encompasses, but is not limited to, thiol esters, inorganic esters, carboxylic esters, unsaturated esters, diazo esters. An example includes, but is not limited to N(1)-methylurocanic acid ester.

The present invention provides a process claiming intermediate compounds. Each of the intermediate compounds is stable. Each intermediate compound having utility as a starting product for the synthesis of the eleutherosides.

The present invention provides a process for the preparation of a Eleutherobin derivative of the formula:

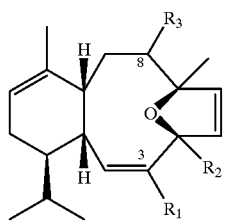

wherein $R_1$ is a hydrogen, ester, nitrile, trif olate or $CH_2$—$R_4$ wherein $R_4$ is a carbohydrate, an ester, an alcohol an amine, an amide, an alkyne,or $C_1$–$C_9$ linear or branched chain alkyl;

R is a linear or branched alkyl moiety;

$R_3$ is an ester, an amide, a carbamate, an acetal compound, an ether or a urethane;

position $C_2$ and $C_3$ is cis or trans;

position $C_8$ is α or β, comprising the steps of:

(a) treating a chiral matrix material with a ketene under suitable conditions to form a compound having the structure:

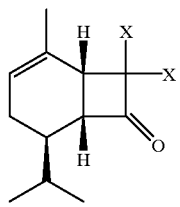

wherein X is a halogen; and (b) Dehalogenating the compound in step (a) under suitable conditions to form a compound having the structure:

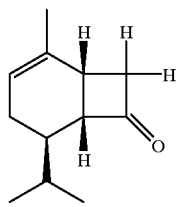

(c) subjecting the compound in step (b) to a Bredereck transformation to form a compound having the structure:

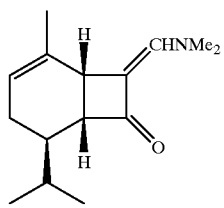

(d) acid catalyzing and fragmenting the compound in step(c) under suitable conditions to form a compound having the structure:

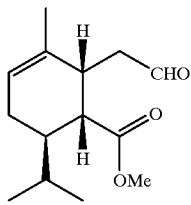

(e) appending a furanoid building block to the compound formed in step (d) under suitable conditions to form a compound having the structure:

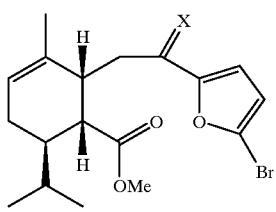

wherein x is α-OH, β-H or α-H, β-OR, (f) protecting the compound formed in step (e) under suitable conditions to form a. compound having the structure:

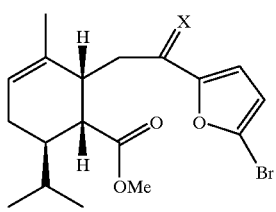

wherein X is α-OTBDPS, β-H or α-H, β-OTBDPS; and (g) expanding the compound in step (f) under suitable conditions to form a compound having the structure:

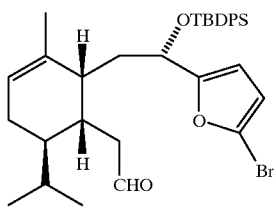

(h) performing a Nozaki-Kishi reaction on the compound in step (g) to form a compound having the structure:

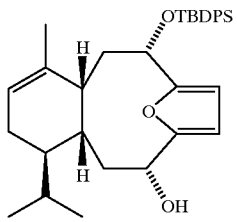

(i) protecting the compound formed in step (h) under suitable conditions to form a compound having the structure:

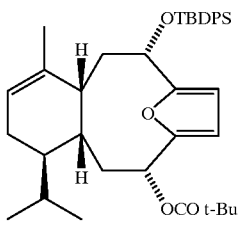

(j) treating the compound in step (i) under conditions suitable to the removal of OTBDPS to form a compound having the structure:

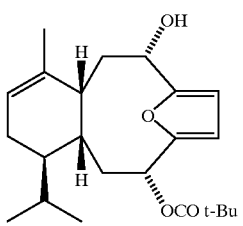

(k) treating the compound in step (j) with dimethyldioxirane under suitable conditions to form a compound having the structure:

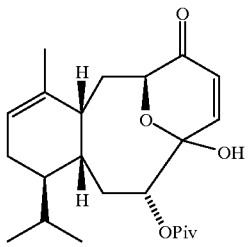

(l) protecting the compound in step (k) under suitable conditions to form a compound having the structure:

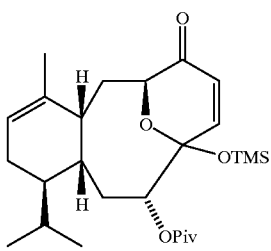

(m) methylating the compound in step (k) or (l) under suitable conditions to form a compound having the structure:

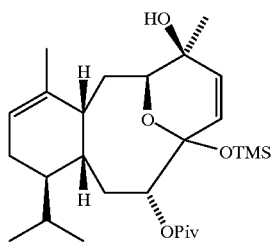

Or

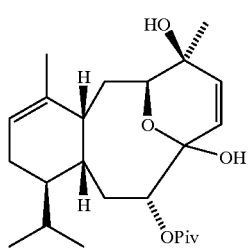

(n) treating compound (2) in step (m) with acetic anhydride under suitable conditions to form a compound having the structure:

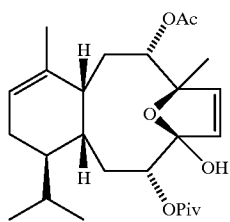

(o) acid catalyzing compound (1) in step (m) under suitable conditions to form a compound having the structure:

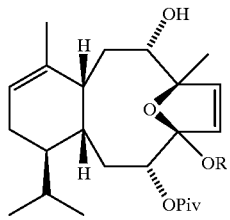

wherein

R is a linear or branched chain alkyl group.

(p) protecting, deprotecting and converting the compound in step (o) under suitable conditions to form a compound having the structure:

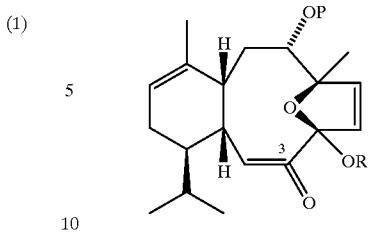

wherein
R is a linear or branched chain alkyl group and P is a protecting group.

(q) treating the compound in step (p) under suitable conditions to form a compound having the structure:

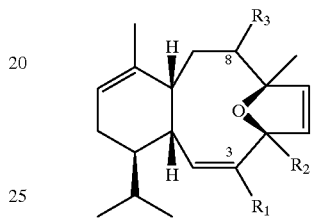

wherein the compound in step (q) can be coupled to a carbohydrate, the carbohydrate consiting of D-arabinose, L-arabinose or D-galactose or a compound having the structure:

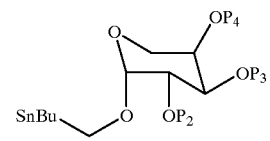

Wherein
$P^2$, $P^3$, $P^4$, are Ac, H or other alkyl, acetyl groups;
$P^2$ is H, SEM, or TBS when $P^3$ and $P^4$ are $C(Me)_2$; and the carbohydrate is synthesized by converting a compound:

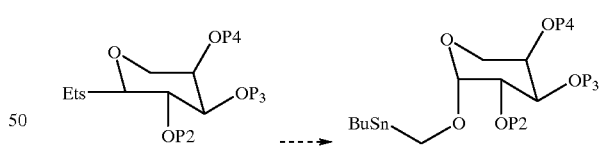

The present invention provides compound having the structure:

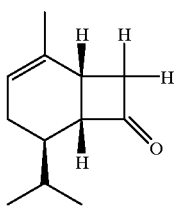

The present invention further provides a compound having the structure:

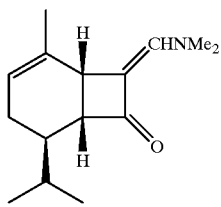

The present invention also provides a compound having the structure:

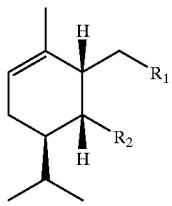

wherein, R$_2$ is a linear or branched alkyl moiety.

The present invention provides a compound having the structure:

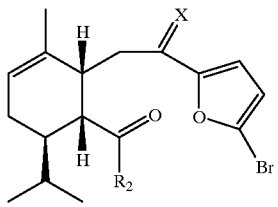

wherein, x is α-OH, β-H or α-H, β-OH; and R$_2$ is a linear or branched alkyl moity.

This invention further provides a compound having the structure:

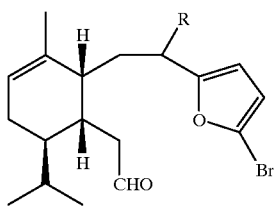

wherein, the configuration of R is α or β and R is OTBDPS or a protecting group.

This invention also provides a compound having the structure:

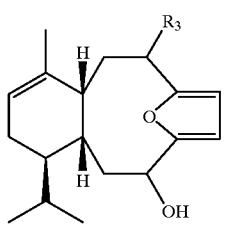

wherein, the configuration of R is α or β and R is OTBDPS or a protecting group.

This invention also provides a compound having the structure:

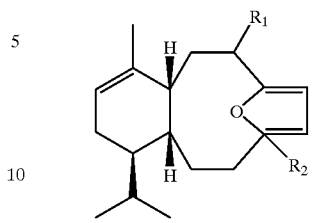

wherein the configuration of R is α or β and R$_2$ is OTBDPS or a protecting group and R$_2$ is OCOt-Bu or a protecting group.

This invention provides a compound having the structure:

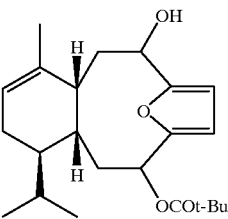

wherein, the configuration of OH is α or β.

This invention further provides a compound having the structure:

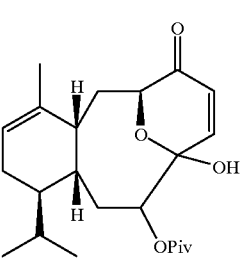

wherein, the configuration is α or β.

This invention further provides a compound having the structure:

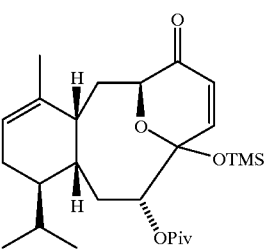

wherein, the configuration is α or β.

This invention also provides a compound having the structure:

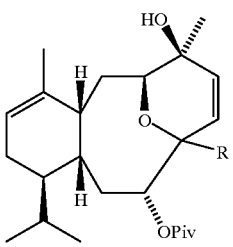

wherein R is OTMS, OH, or a protected hydroxyl group; and the compound is α or β.

This invention further provides a compound having the structure:

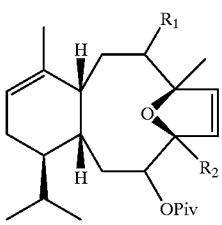

wherein $R_1$ is OAc or OH and$_2$ R is OH or a linear or branched alkyl protected hydroxyl groups.

The present invention provides a compound having the structure:

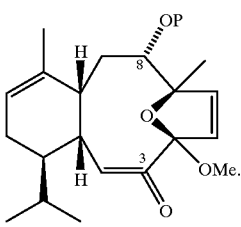

The present invention provides a method for inhibiting growth of cancerous cells comprising contacting an amount of the compound to inhibit, reduce, or cause remission of the cancer of a Eleutherobin analogue effective to inhibit the growth of said cells.

The present invention provides a method for treating cancer wherein, the cancer is a cancer of the breast, colon, lung, liver, brain or ovary. in a subject which comprises administering to the subject wherein, the administration comprises epidural, intraperitoneal, intramuscular, subcutaneous or intravenous injection; infusion; or topical, nasal, oral, anal, ocular or otic delivery, a therapeutically effective amount comprising an amount of the compound to inhibit, reduce, or cause remission of the cancer wherein the amount is from about 0.02 to about 10 mg/kg body weight of an Eleutherobin analogues.

Step (a) is performed with a chiral matrix material such as R-(−)-α- phellandrene using a catalyst such as zinc or nickel chromium, under various conditions known in the art to effect the transformation, preferably under conditions such as sonication at 0° C. using a reagent such as trichloroacetyl chloride and a solvent such as $Et_2O$.

Step (c) is performed with material such as (t-Bu(O)CH$(NM_2)_2$ under various conditions known in the art to effect the transformation, preferably under conditions at or about 60° C.

Step (e) is performed using a furanoid building block such as 2,5-dibromofuran under various conditions known in the art to effect the transformation.

Step (h) is performed using Nozaki-Kishi reaction, using various conditions known in the art to effect the transformation.

Step (q) is performed using a metal catalyst, a carbohydrate such as D-arabinose and a modified Stille coupling, under various conditions known in the art to effect the transformation.

The present invention provides a method for treating cancer in a subject which comprises administering to the subject a therapeutically effective amount of a Eleutherobin analogues.

The cancer is a cancer that includes but is not limited to carcinoma of the breast, colon, lung, liver, brain or ovary.

The therapeutically effective amount comprises an amount of the compound to inhibit, reduce, or cause remission of the cancer. Optimal dosages to be administered may be determined by those skilled in the art, and will vary with the particular compound used, the strength of the preparation, the mode of administration, and the advancement of the disease condition.

The administration of a Eleutherobin analogue may be by any conventional route of administration including but not limited to epidural, intraperitoneal, intramuscular, subcutaneous or intravenous injection; infusion; or topical, nasal, oral, anal, ocular or otic delivery.

Microtubules are important components of the eukaryotic cytoskeleton that are essential for separation of the duplicated chromosome pairs during mitosis. They also have significant functions in interphase cells that include intracellular transport, maintenance of cell shape, locomotion, and transmission of signals between cell surface receptors and nuclear effectors (1). The multi functionality of the microtubule system makes it an attractive target in cancer chemotherapy.

The functional diversity of the microtubule system is exemplified by the mechanisms of action of the antitumor drug Taxol (2), isolated in 1971 from the Pacific Yew tree, Taxus brevifolia. The primary target of Taxol is the tubulin/microtubule system. The drug interacts with the N-terminal 31 amino acids (3), and amino acids 217–231 (4) of the β-tubulin subunit. Taxol promotes hyperstabilization of microtubules which are resistant to depolymerization by either calcium of cold (5), conditions that depolymerize normal microtubules. This results in microtubule bundling and arrest of cells in mitosis (6), eventually leading to cell death. It has been demonstrated in HeLa cells that low concentrations of Taxol suppresses microtubule dynamics, thereby interrupting normal mitosis (7). Evidence indicates that Taxol also modulates specific intracellular signaling events including the induction of tumor necrosis factor alpha (TNF-α), and increased tyrosine phosphorylation of proteins, including MAPK (8–11). Extended exposure of cells to Taxol induces DNA fragmentation, indicating that the cells undergo apoptosis (12,13).

The approval of Taxol for the treatment of breast and ovarian carcinomas has led to renewed interest in the microtubule as an important target for the development of new chemotherapeutic drugs, and this has inspired a search for novel natural compounds that mimic the activity of Taxol. One such compound, eleutherobin, was isolated from the Eleutherobia species of a rare marine soft coral and its structure has been delineated (14). It has been reported that eleutherobin has a mechanism of action similar to that of Taxol in that it potentiates the assembly of stable microtubules resistant to depolymerization (15). Due to the limited availability of natural eleutherobin, and its potential as an anticancer drug, it was rapidly synthesized in the laboratory (16–19).

Reported in this study is the in vitro biological profiles of five eleutherobin analogues. Three of the compounds lack the carbohydrate domain and one lacks the C8 N(1)-methylurocanic acid. The objectives of this study were to define a structure-activity profile for eleutherobin to aid in the elucidation of a common pharmacophore between Taxol and eleutherobin and the development of more potent analogs of such drugs.

This invention will be better understood from the Experimental Details which follow. However, one skilled in the art will readily appreciate that the specific methods and results discussed are merely illustrative of the invention as described more fully in the claims which follow therafter.

Experimental Details

All air and moisture sensitive reactions were performed in a flame-dried apparatus under a nitrogen atmosphere unless otherwise noted- Air-sensitive liquids and solutions were transferred via syringe or cannula. Unless otherwise noted, all solvents and reagents were commercial grade and were used as sold.

High resolution mass spectra (HRMS) were determined by electron impact ionization (EI) on a JEOL JMS-DX 303HF mass spectrometer with perfluorokerosene (PFK) as an internal standard.

Eleutherobin and its derivatives were synthesized as described (18,19). Taxol was obtained from the Drug Development Branch, National Cancer Institute (Bethesda, Md.). All compounds were dissolved in dimethyl sulfoxide (Sigma Chemical Co., St. Louis, Mo.) at stock concentrations of 5 mM and stored at −20° C. All control samples contained an equal volume of DMSO. GTP was obtained from Sigma Chemical Co. And dissolved in sterile distilled water at a concentration of 10 mM and stored at −20° C. Microtubule protein was purified from calf brains by two cycles of temperature-dependent assembly and disassembly (20) and stored in liquid nitrogen prior to use. The anti-mouse β-tubulin monoclonal antibody T-4026 was obtained from Sigma Chemical Co.

Human non-small cell lung carcinoma cells, A549, were maintained in RPMI 1640 containing 10% fetal bovine serum and 1% penicillin-streptomycin (Gibco Laboratories, Grand Island N.Y.) at 37° C. in 7% $CO_2$. The Taxol-resistant cell line A549-T12 was selected for resistance to Taxol and maintained in a final concentration of 12 nM drug (21). Human ovarian carcinoma cells SKOV3 and the MDR variant SKVBL (obtained from Dr. V. Ling) were maintained in α-mem plus ribonucleotides, deoxynucleotides, 15% fetal bovine serum and 1% penicillin-streptomycin (Gibco Laboratories) at 37° C. in 5% $CO_2$. SKVBL cells were maintained in imM vinblastine (Sigma Chemical Co.).

Taxol-resistant and sensitive cell lines were seeded into 12-well plates at a density of $5\times10^4$ cells per well and allowed a period of 12 h for attachment prior to treatment. Cells were exposed to 10-fold serial dilutions of each compound ($10^{-10}$ to $10^{-6}$ M) for 72 h. Cells were then trypsinized and counted (Coulter counter model ZF0031, Coulter Corp., Miami, Fla.). The $IC_{50}$ was determined by plotting cell number against log of the drug concentration and this was used to determine the concentration of compound resulting in 50% growth inhibition compared to untreated cells. Each cell line was assayed in a minimum of 3 independent experiments with each compound and the results expressed as the mean $IC_{50}$.

The ability of each compound to polymerize tubulin was evaluated by recording the change in turbidity of microtubule protein at 350 nm for 80 min in a spectrophotometer (UVIKON, Research Instruments Int., SD, Calif.). One mg of purified microtubule protein was diluted in assembly buffer containing 0.1 M MES, 1 mM EGTA, 0.5 mM $MgCl_2$ and 3 M glycerol, pH 6.6. All compounds were evaluated at a concentration of 10 $\mu$M at 37° C. GTP was used at a final concentration of 1 mM. Microtubule stability was assessed by the addition of 10 mM $Ca^{++}$. changes from t=0–10 min were used to calculate initial slopes from the linear portion of each curve. These values were used to calculate the activity of each compound (relative to the activity of Taxol which was assigned a value of 100%).

NIH 3T3 cells were grown to subconfluency on glass converslips in 35 mm plastic petri dishes. Cells were exposed to 2 $\mu$M of Taxol and each of the experimental compounds for 5.5 h at 37° C., rinsed twice in PBS and extracted with 0.5% Triton-X-100 in microtubule stabilizing buffer (PEM) (100 mM PIPES, 2 mM EGTA and 2 mM $MgCl_2$, pH 6.8) for 4 min. Following a wash in PEM, the cells were fixed for 40 min at room temperature in 3% formaldehyde in PEM followed by incubation in 0.1 M glycine in PBS for 10 min and washing (four times) in PEM containing 5 $\mu$M EGTA. Following blocking in 20% normal goat serum (NGS) for 30 min at room temperature, cells were incubated for 1 h at 37° C. with a 1:100 dilution of β-tubulin mAb diluted in 10% NGS, washed twice in 1% BSA, once in PBS and three times in 1% BSA. Cells were then incubated in a 1:200 dilution of the secondary fluorophore antibody, IndocarbocyanineCY3 (Jackson Immunoresearch Laboratories Inc., Pa.) in 20% NGS for 20 min at room temperature. Finally cells were washed three times in 1% BSA and the dried slides mounted in 30% glycerol in PBS containing β-phenylene diamine (1 mg/ml). Fixed slides were examined using a Zeiss Axioskop microscope.

Results and Discussion

Synthesis of Eleutherubin Core

The chiral matrix material selected for elaboration is the readily available R-(−)-α-phellandrene(FIG. 2 step 4)(35). This compound undergoes cycloaddition with a ketene derivative (dichloroketene). A $C_1$ fragment is than appended to the modified cyclobutanone cycloadduct, and the ring is fragmented to produce a system of the type (FIG. 2 step 5) with differentiated arms for subsequent elaboration.

Figure 2:
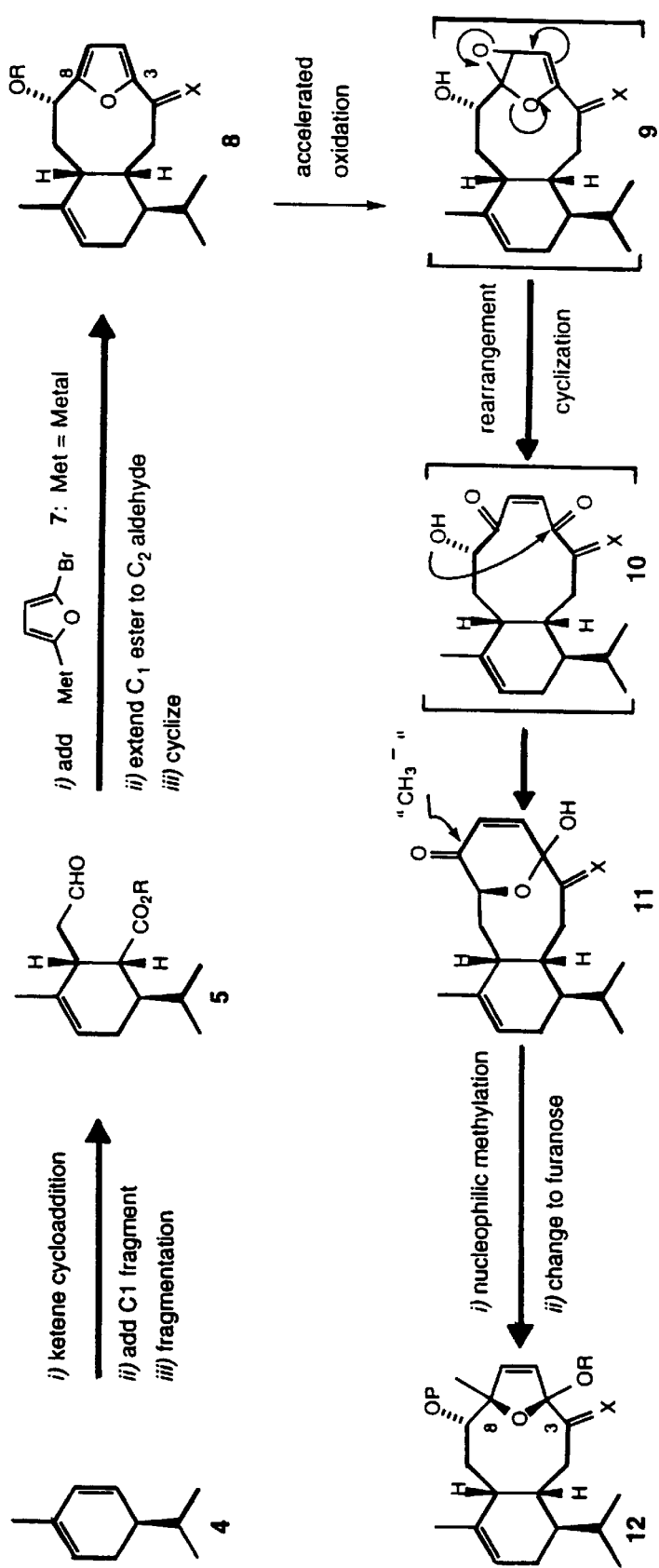
FIG. 2 shows the underlying logic of the synthetic plan.

A furanoid building block (2,5 -dibromofuran) (FIG. 2 step 6) (36) provides system (FIG. 2 step 7) as a nucleophile. The remaining furyl-bromine bond constitutes a latent form of carbon nucleophilicity, to be exploted later (vide infra.) In the first coupling event, system (FIG. 2 step 7) the furanoid building block is delivered to the aldehyde function of (FIG. 2 step 5). Next, the "arm" extending from the the ester linkage is expanded by one carbon through a cyanation reaction. An eventual acetaldehyde appendage is coupled to the "bromofuryl" carbon ($C_4$) producing a compound of type (FIG. 2 step 8), a highly strained 2,5 -furano[6] phane. In this construction, the two benzylic oxygen functions at $C_8$ and $C_3$ in (FIG. 2 step 8) are presented in differentiated forms. The free hydroxyl group at $C_8$ accelerates oxidation of the proximal furan. Following bond reorganization (FIG. 2 steps 9→10), ring formation between the hydroxyl and appropriate keto-group leads to a pyranose of the type (FIG. 2 step 11). In this system, the $C_7$ keto-group, destined for nucleophilic methylation, has been uniquely identified. Moreover, in (FIG. 2 step 11)), the setting for the entry of the methyl group in the desired stereochemical sense had been established, since reaction would be directed anti to the more sterically demanding five-carbon bridge. Following suitable manipulations, the pyranose ring in (FIG. 2 step 11)) is rearranged to a furanose, thereby exposing the two oxygen atoms projecting from $C_3$ and $C_9$ of the skeleton in differentiated form (FIG. 2 step 12).

Figure 3:
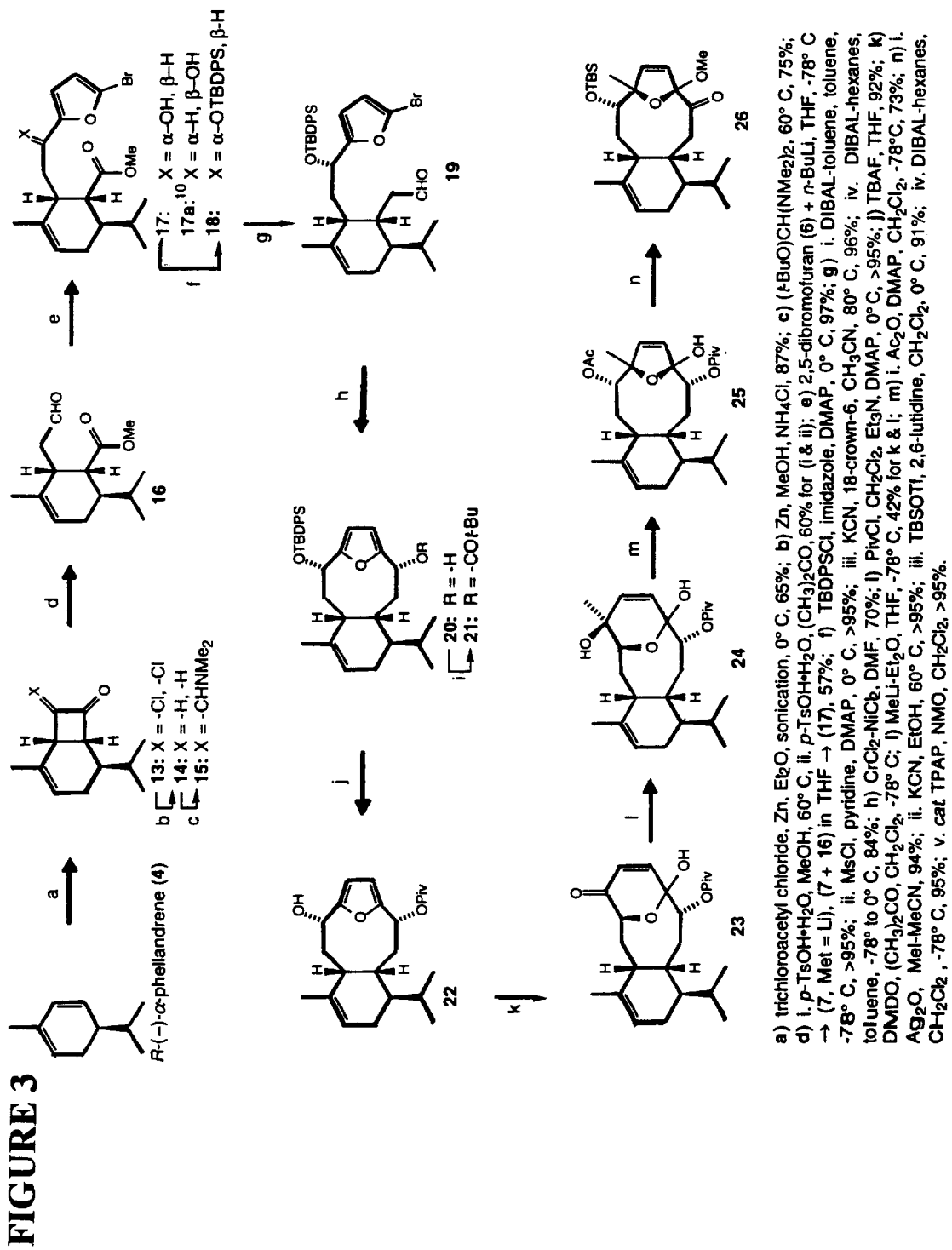
FIG. 3 illustrates the construction of an eleutheside skeleton.
Figure 4:
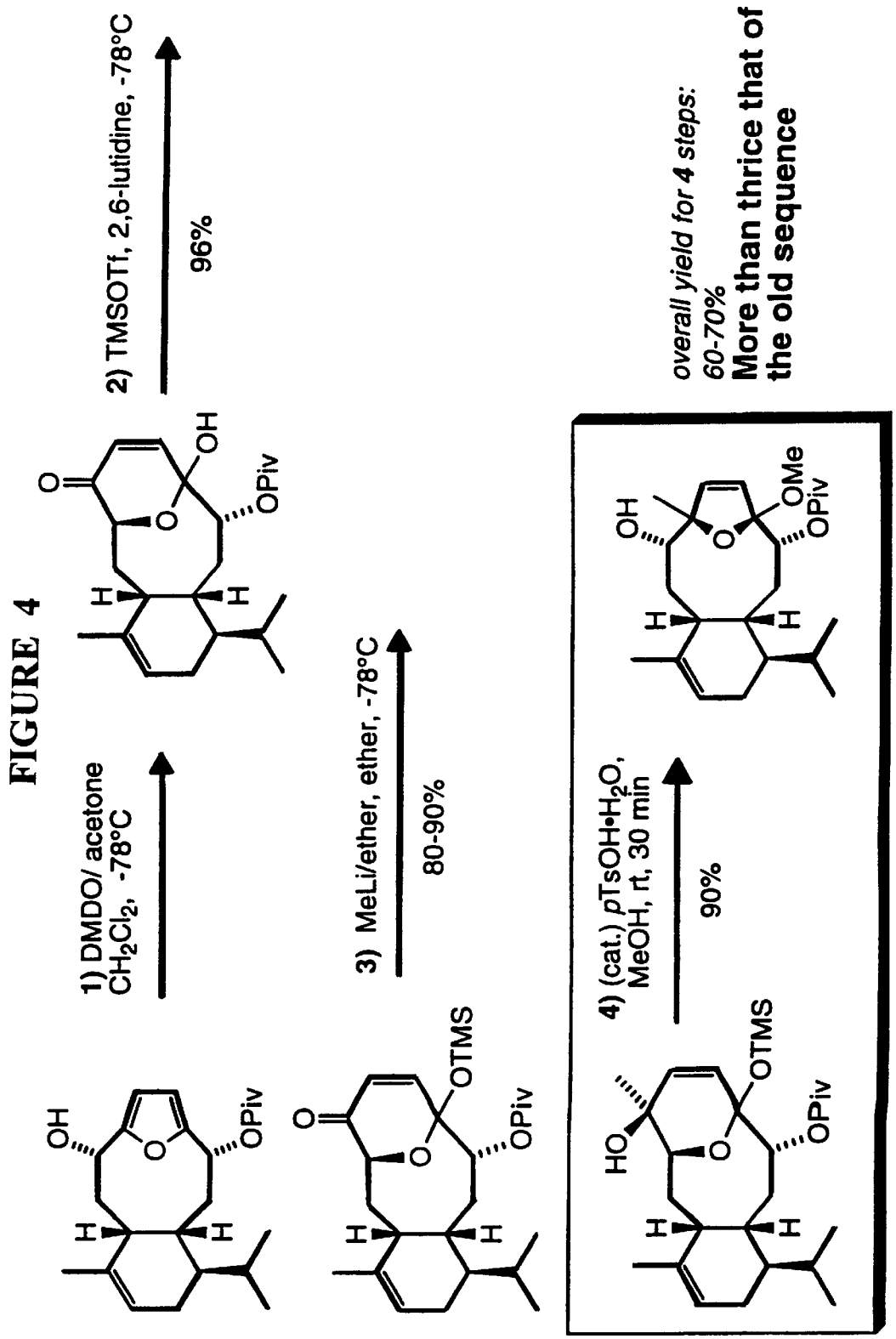
FIG. 4 illustrates the construction of an eleutheside skeleton using a new sequence.
Figure 5:
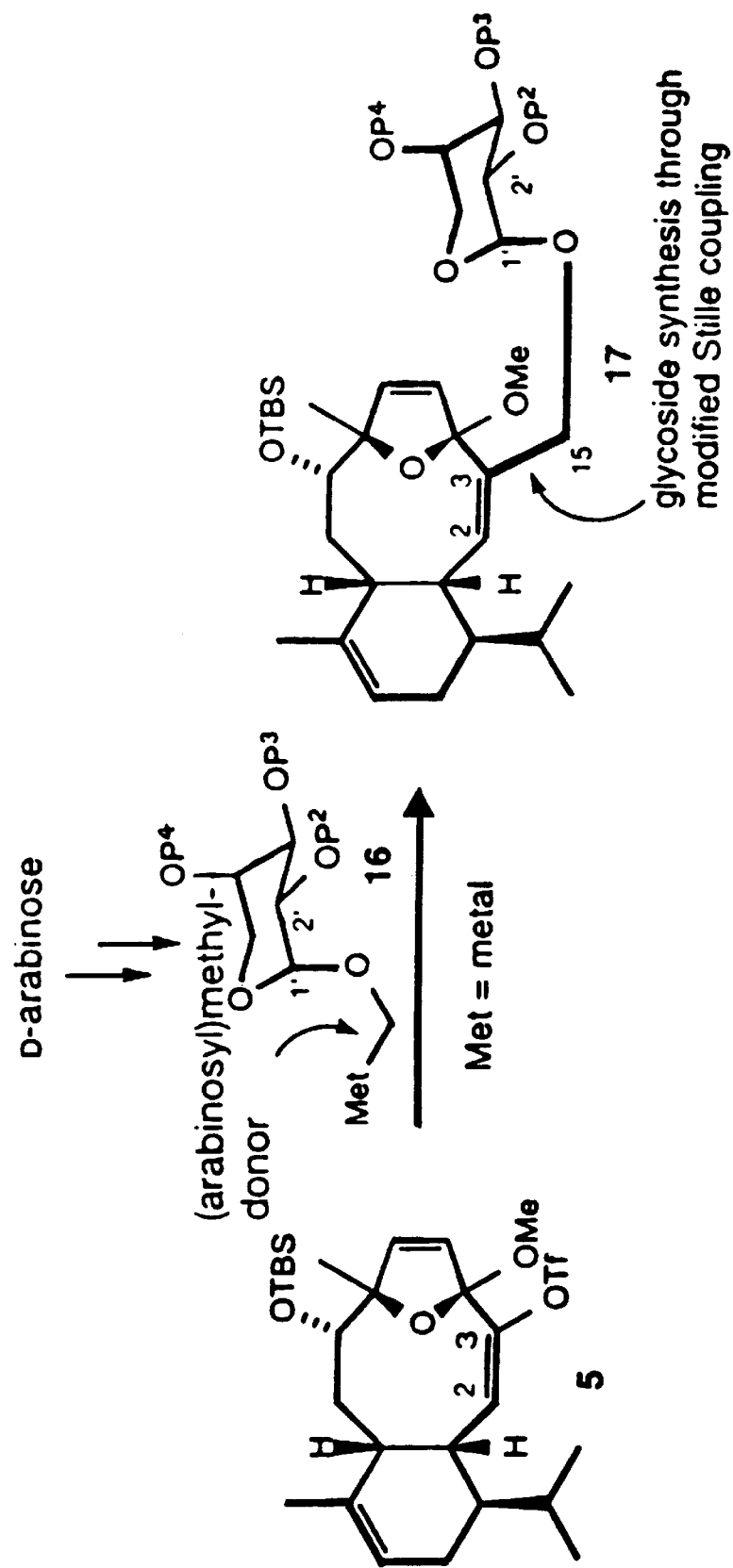
FIG. 5 illustrates the glycosylation strategies to synthesis of eleutherobin.

In the actual steps employed for building the eleutheside to be noted is the regiospecificity of the dichloroketene cycloaddition reaction (the stereoselctivity in the indicated sense is 9:1)(37). The product (FIG. 3 step 14) resulting from the dechlorination of the initial cycloadduct (FIG. 3 step 13), is subjected to a Bredereck type transformation (38), leading to (FIG. 3 step 15). At this stage, an acid catalyzed fragmentation of the cyclobutanone (37, 38), exposes an acetaldehyde residue (wherein the formyl group corresponds to the eventual $C_8$) and the methyl ester corresponding to C2 (FIG. 3 step 16). Monolithiation of 2,5-dibromofuran, (FIG. 3 step 6) and appending the interesting species (FIG. 3 step 7) (Met=Li), to the aldehyde (FIG. 3 step 16), thereby produces compound (FIG. 3 step 1) and its redeemable $C_8$ epimer (FIG. 3 step 17a). Following suitable protection, (FIG. 3 step 18) was obtained. (40) At this point, the one carbon ester was expanded to a two carbon aldehyde (FIG. 3 step 19), in which the formyl carbon corresponds to the eventual $C_3$ of the eleuthesides. The critical step leading to metacyclophane (FIG. 3 step 20) was the stereoselective Nozaki-Kishi (41) reaction. The hydroxyl group at the future $C_3$ was protected as its pivaloate ester (FIG. 3 step 21).

The construction of the eleutheside skeleton from this position involves treatment of (FIG. 3 step 22) with dimethyldioxirane generation of an epoxide. Following suitable bond reorganizations, passing through presumed diketone type (FIG. 2 step 10), pyranose (FIG. 3 step 23) was generated. The predicted stereoselective neucleophilic methylation of the keto function was achieved with methyllithium, giving rise to (FIG. 3 step 24). On treatment of the latter compound with acetic anhydride, selective acetylatability of the masked secondary alchohol at $C_8$, paves the way for cyclization of the tertiary alcohol (corresponding to $C_8$ of the future eleutheside) into the carbonyl group of the enone of the open form (FIG. 3 step 25). All structural assignments asserted thusfar, are corroborated by a crystallographic determination. The compound (FIG. 3 step 25) has been advanced in several directs, including the generation of the flexible platform compound, ketone (FIG. 3 step 26) for producing analogues.

Total Synthesis of Eleutherobin

Figure 10:
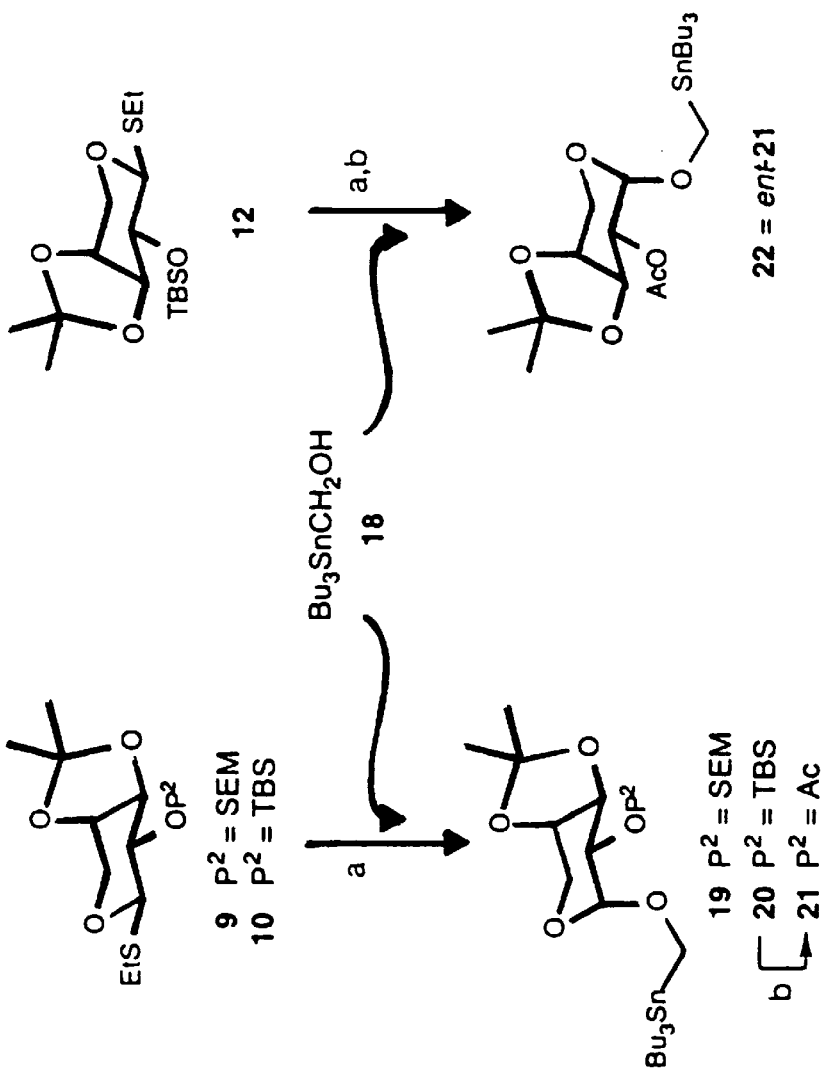
Figure 10B:
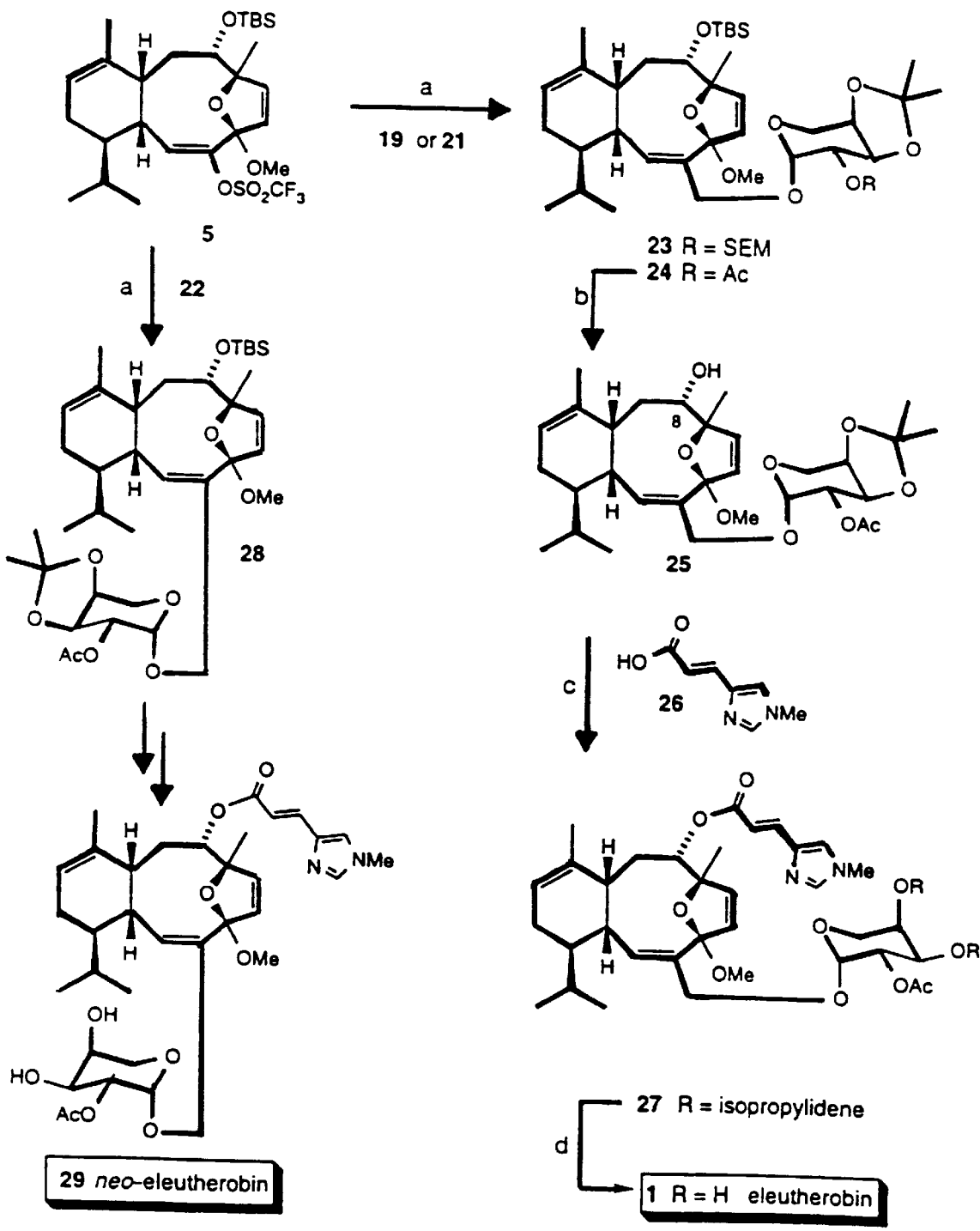

The addition of the carbohydrate sectors of eleutherobin to the platform compound above was accomplished by merging the aglycone and carbohydrate domaines. (Arabinosyl)methyl donors (FIG. 10 step 19 and 20 scheme 4) were synthesized using a classical donor in a Lonn-Garegg glycosylation (42) with tri-n-butylstannylmethanol (FIG. 10 step 18 scheme 4) (43). A 93% yield of a 1:1 mixture of glycosides readily separable into its components was obtained. The β-form was of interest (FIG. 10 step 19 scheme 4) (44). The thioethyl donor (FIG. 10 step 10 scheme 4) served to glycosylate (FIG. 10 step 18 scheme 4), affording a 1:1 mixture of separable glycosides. Cleavage of the TBS group of the β-glycoside (FIG. 10 step 20 scheme 4) and installation of an acetate led to (FIG. 10 step 21 scheme 4). In an identical way, the ent-(arabinosyl)-methyl donor (FIG. 10 step 22 scheme 4) was prepared from (FIG. 10 step 12 scheme 4).

Modified Stille coupling of vinyl triflate with (FIG. 10 step 19 or 21 scheme 4) gave rise, in 40–50% yields of (FIG. 10 step 23 and 24 scheme 5) respectively. From compound (FIG. 10 step 24 scheme 5) the pathway to eleutherobin was straightforward. The hydroxy group at C8 was liberated (FIG. 10 step 25 scheme 5) and acylated with (E)-N(1)-methylurocanic acid (FIG. 10 step 26 scheme 5) (45) to afford (FIG. 10 step 27 scheme 5), as shown. Removal of the acetonide protecting group, released eleuthobin itself.

The 500 Mhz NMR spectrum (and optical rotation) of fully synthetic eleutherobin corresponded very closely to the spectrum of natural eleutherobin, recorded and. forwarded to us by Penical et al. (31) A sample of naturally derived eleutherobin was not available for direct comparison in our laboratory.

At this stage, we could not be confident that the spectral consequences of having an enantiomeric L-arabinose-derived sugar domain attached to the same aglycone (i.e. neoeleutherobin, vide infra) would be significant. If the two domains were virtually noninteractive, the differences between the two permutations might be difficultly discernible. To check this point, we proceeded to synthesize the only viable alternative version of eleutherobin. For this purpose, (FIG. 10 step 22 scheme 5) was coupled with vinyl triflate (FIG. 10 step 5 scheme 4) to produce (FIG. 10 step 28 scheme 5). Following an identical series of steps used in the previous series, compound (FIG. 10 step 29 scheme 5) was in hand. (32)

Examination of the 500 Mhz NMR spectrum of (FIG. 10 step 29 scheme 5), which we call neoeleutherobin, revealed small, but clear-cut, differences with the spectrum of eleutherobin itself, provided by Fenical et al. Hence, we can rigorously assert that the relative chiralities of the aglycone and arabinose domains of eleutherobin, and that the total synthesis of eleutherobin has been accomplished.

Structure-Activity Profile

Figure 6A:
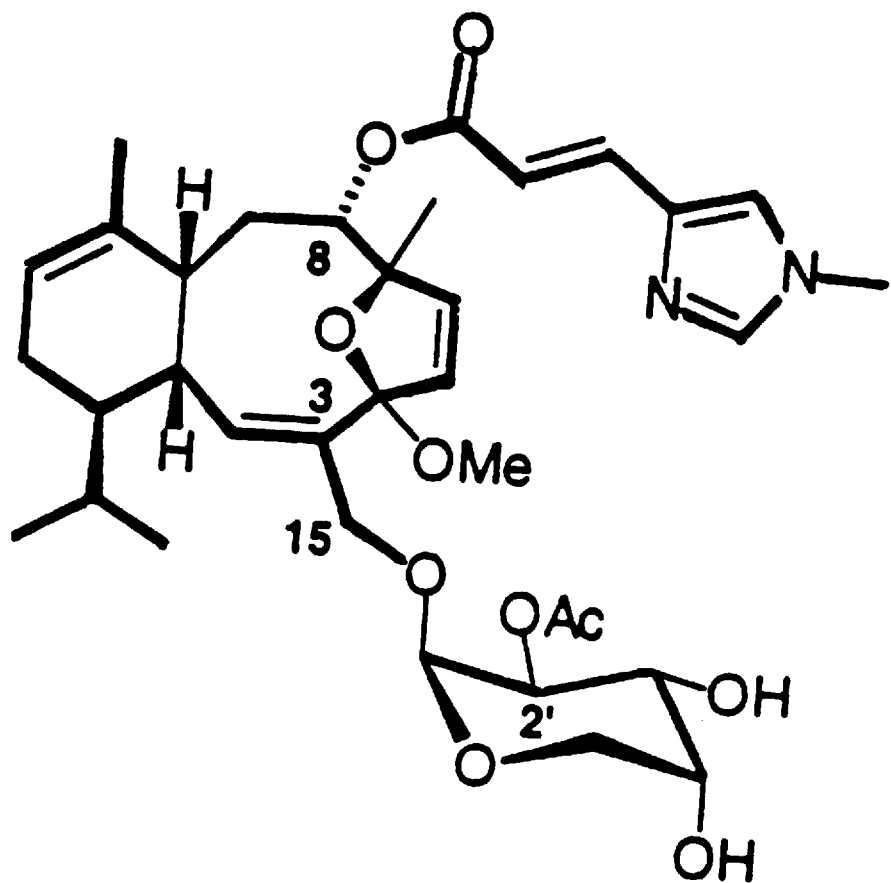
FIG. 6 chemical structures of eleutherobin and analogs.
Figure 6B:
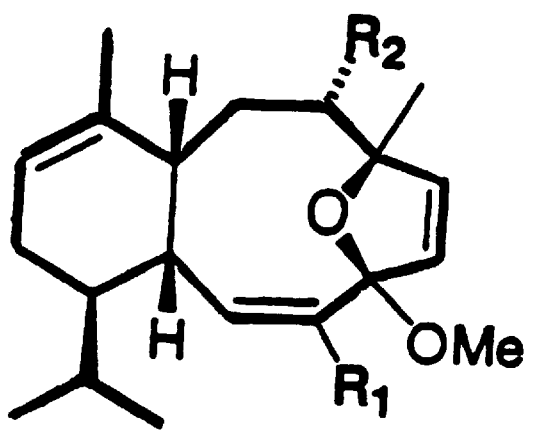

The cytotoxic efficacy of eleutherobin and its derivatives (FIG. 6) was evaluated in two drug sensitive human cancer cell lines and their Taxol-resistant counterparts. The results are summarized in Table I in order of decreasing potency. A549 -T12 cells are 7 -fold resistant to Taxol compared to A549 cells, and do not express MDR1, hence excluding P-glycoprotein as a mechanism of resistance. Although the mechanism of resistance has not been fully defined for A549 -T12, an investigation of the mRNA expression of β-tubulin isotypes revealed an altered ratio of distinct isotypes in Taxol-resistant A549 -T12 cells (21). The Taxol-resistant cell line SKVBL overexpresses high levels of P-glycoprotein (22). In both sensitive cell lines, eleutherobin was 3 -fold less potent than Taxol, although the $IC_{50}$ values obtained for eleutherobin were within the nM range. Neo-eleutherobin was 14–20 fold less active than eleutherobin. The only difference between the two agents is the enantiomeric relationship in the carbohydrate (2'-acetylarabinose) sector (FIG. 6). In a potentially important observation, neither eleutherobin nor neo-eleutherobin displayed cross-resistance in the Taxol-resistant A549 -T12 cell line, suggesting that the mechanism of resistance in this cell line is specific to Taxol. In contrast, both compounds demonstrated high resistance in SKVBL cells expressing MDR1, greater or equal to 1052- and 75-fold, respectively. This cell line expressed high levels of MDR1 resulting in Taxol-resistance equal or greater than 1666 -fold compared to the Taxol-sensitive SKOV3 cell line. These results suggest that both eleutherobin and neo-eleutherobin, like Taxol, are excellent substrates for P-glycoprotein.

The compounds SKBII.294 and 296 (FIG. 6), which lack the carbohydrate domain, were less cytotoxic than either eleutherobin or neo-eleutherobin. Compound SKBII.294 was more cytotoxic than SKBII.296 indicating that subtle alterations at the C3 position influence the overall activity of these compounds. Compound SKBII.298, which is structurally similar to SKBII.294 but lacks the C15 O-acetyl group was considerably less cytotoxic (in the μM range). Compound SKBIII.13 in which the N(1)-methylurocanic acid moiety has been removed was basically inactive by all parameters tested.

Figure 7:
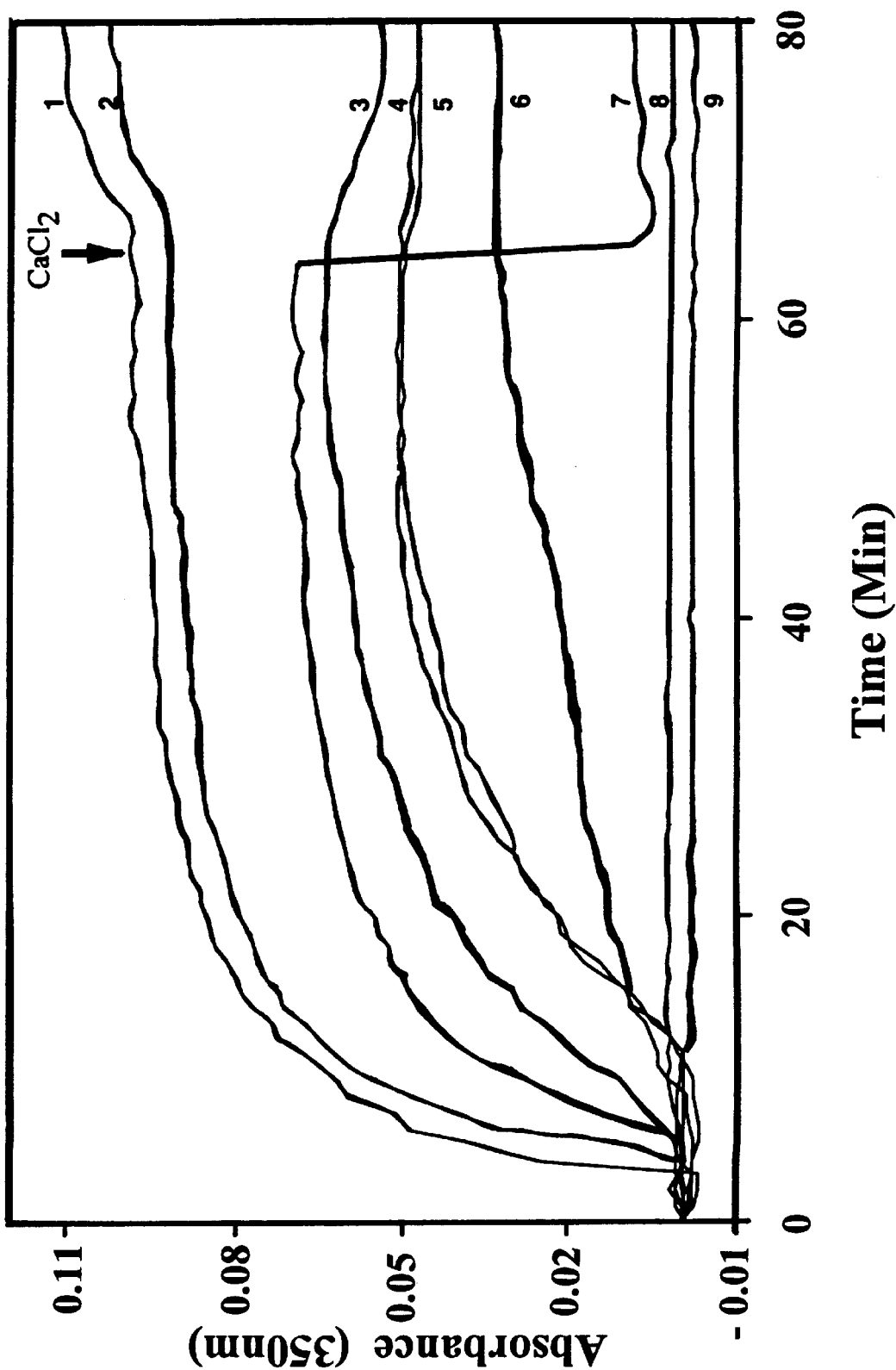
FIG. 7 ploymerization of brain tubulin at 37° C. in the absence of GTP, by 10 µM 1)Taxol, 2) eleutherobin, 3) neo-eleutherobin, 4) SKBII-294, 5)SKBII.296, 6) SKBII.298, 7)1 mM GTP, 8)SKBIII.13 and 9)DMSO control. 10 mMCaCl$_2$ was added to each cuvette at the time indicated by the arrow.

The ability of each compound to polymerize and/or stabilize microtubules was assessed (FIG. 7). To investigate whether eleutherobin and its derivatives shared the microtubule stabilizing properties of Taxol, 10 mM $CaCl_2$ was added to each sample after maximum microtubule polymerization occurred, and the effects on turbidity recorded spectrophotometrically. A positive control was included in which 1 mM GTP was used to confirm the ability of GTP-stabilized microtubules to undergo $Ca^{++}$ induced depolymerization.

Figure 8:
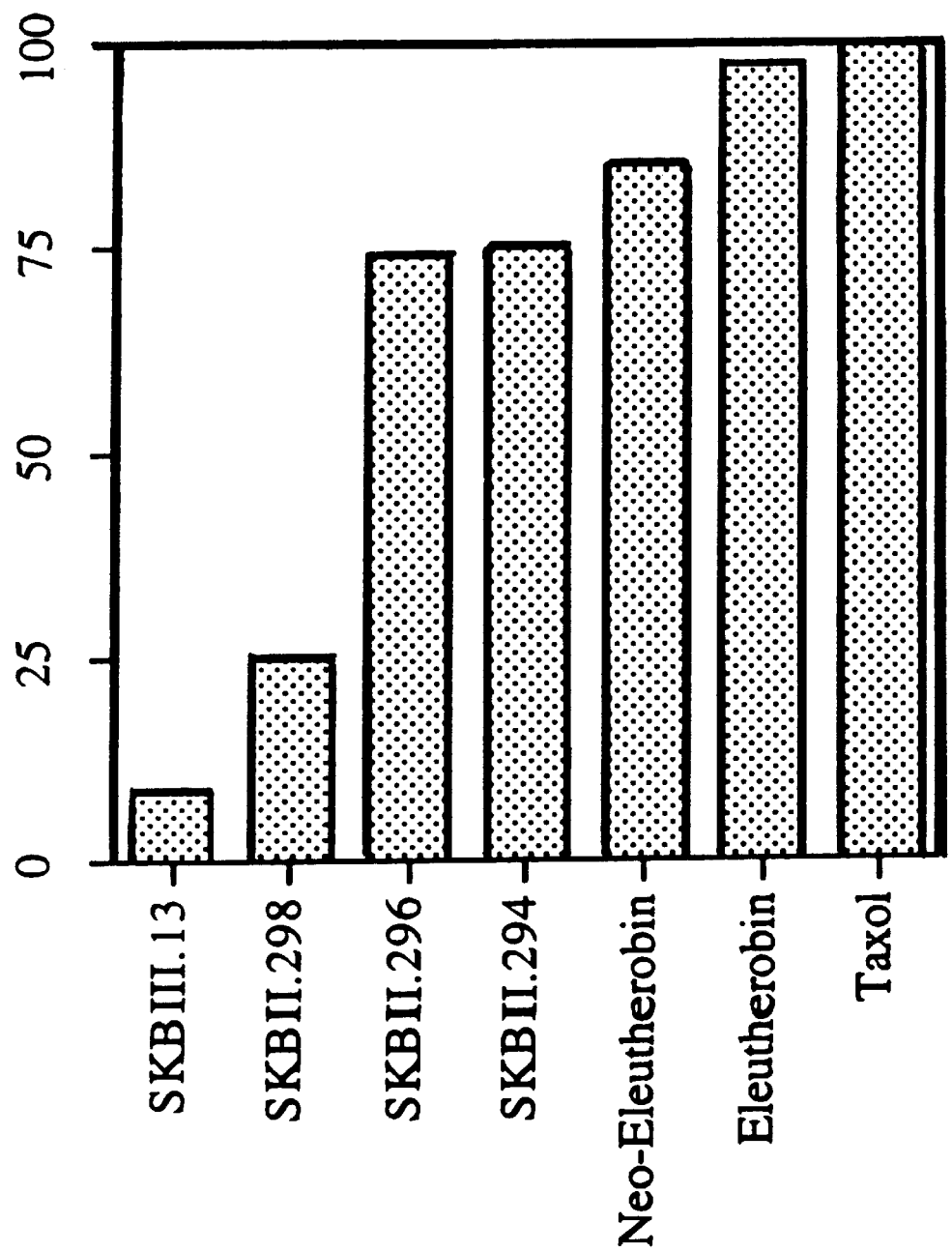
FIG. 8 relative polymerization activity of eleutherobin and its derivatives. Values represent the slope of each curve at $A_{350\ nm}$ from t=0–10 minutes (FIG. 7) relative to Taxol.
Figure 9A:
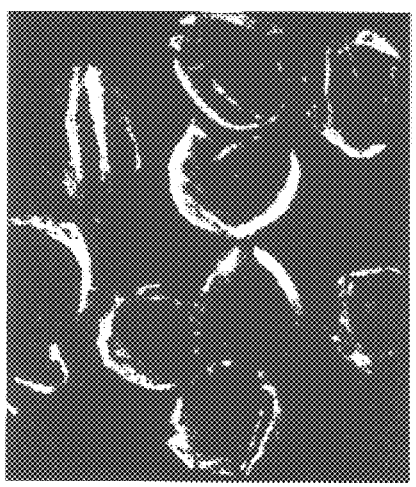
FIG. 9 immunofluorescence images NIH3T3 cells labeled with β-tubulin antibody following exposure to different drugs. A)DMSO; B)2 μM Taxol; C)2 μM eleutherobin; D)2 μM neo-eleutherobin; E)2 μM SKBII.294; F)2 μM SKBIII.13.
Figure 9B:
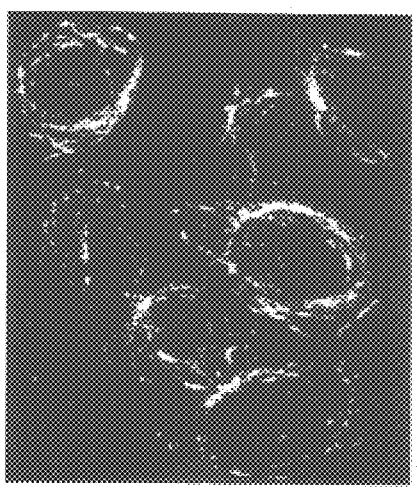
Figure 9C:
Figure 9D:
Figure 9E:
Figure 9F:

Eleutherobin (10 μM), was slightly less active than Taxol at 37° C., exhibiting 94% of the polymerization activity of 10 μM Taxol. The drug, like Taxol stabilized microtubules against $Ca^{++}$-induced depolymerization. The addition of $CA^{++}$ to Taxol- and eleutherobin-polymerized microtubules resulted in a small increase in turbidity which may be due to some $Ca^{++}$ precipitation. Neo-eleutherobin (10 μM) exhibited 69% of the microtubule polymerization activity of the parent compound eleutherobin, and the microtubules formed also resisted $Ca^{++}$-induced depolymerization. The activities of the compounds SKBII.294 and 296 were identical in the tubulin polymerization assay. This can be seen for the extent of polymerization (FIG. 7) and the initial rate of polymerization (FIG. 8). Both compounds retained 54% of the activity of eleutherobin, whereas SKBII.298 retained only 36% of the activity of eleutherobin. It should be noted that compounds SKBII.294, 296 and 298 had reduced solubility compared to eleutherobin. This resulted in an increase in turbidity at 350 nm when each of these compounds was added to the microtubule protein in MES buffer. This problem was resolved by measuring the small absorbance of each compound in MES buffer alone at 350 nm and subtracting this baseline value from subsequent tubulin polymerization curves.

Compound SKBIII.13, bearing an intact sugar but lacking the urocanic acid moiety, was inactive in tubulin polymerization assays. The ability of this compound to stabilize microtubules formed in the presence of GTP was examined. After a period of 15 min, 10 mM $Ca^{++}$ was added and the change in turbidity recorded. Compound SKBIII.13 was unable to stabilize GTP-polymerized microtubules against $Ca^{++}$ induced depolymerization (data not shown).

The polymerization activity of these compounds was also assessed by determining the slope of the linear portion of each curve at $A_{350\ nm}$ (t=0–10 min), and expressing this relative to Taxol (which was assigned a value of 100% (FIG. 8). The order of activity of eleutherobin and derivatives using this method, corroborates the results obtained from cytotoxicity studies.

TABLE 1

Cytotoxicity of Eleutherobin and its Derivatives in Taxol-sensitive and Taxol-resistant human cancer cell lines

| | Lung Carcinoma A549 | | Ovarian Carcinoma SKOV3 | |
|---|---|---|---|---|
| DRUG | Sensitive | Resistant | Sensitive | Resistant |
| Taxol | 2 | 14.2 (7.1)[b] | 3 | >5000(≧1666)[b] |
| Eleutherobin | 6 | 12.2 (1.9) | 9.5 | >1000(≧1052) |

TABLE 1-continued

Cytotoxicity of Eleutherobin and its Derivatives in Taxol-sensitive and Taxol-resistant human cancer cell lines

| | Lung Carcinoma A549 | | $IC_{50}(nM)$ Ovarian Carcinoma SKOV3 | |
|---|---|---|---|---|
| DRUG | Sensitive | Resistant | Sensitive | Resistant |
| Neo-Eleutherobin | 125 | 146 (1.2) | 134 | >1000(≧74.6) |
| SKBII.294 | 152 | 162 (1.1) | 307 | 1036 (3.4) |
| SKBII.296 | 400 | 4000(10) | 1626 | 1350 (0.8) |
| SKBII.298 | 1059 | ND | >5000 | ND |
| SKBIII.13 | 4150 | ND | >5000 | ND |

[a]Cytotoxicity determined by counting cells after 72 h drug exposure. Each value represents the mean IC50 derived from at least three independent experiments.
[b]Value in parenthesis is the fold resistance of the compound relative to the parental cell line.
ND, Not determined This study describes the structure-activity profile of five eleutherobin analogs based on their cytotoxicity, ability to polymerize and stabilize microtubules in the absence of GTP and to induce microtubule bundle formation in cells. In addition, their cross-resistance in two Taxol-resistant cell lines whose resistance arises from two different mechanisms has been examined.

Neo-eleutherobin, an analog that bears a carbohydrate domain (L-β-2'-O-acetyl arabinose) enantiomeric with that of the natural product, was less active than eleutherobin in all of the parameters examined. Therefore, the nature of the sugar moiety, while not absolutely critical for activity, definitely influences the potency of the compound. In Taxol-resistance SKVBL cells that overproduce P-glycoprotein, both eleutherobin and neo-eleutherobin demonstrated cross-resistance, suggesting that they are substrates for P-glycoprotein. However, neither of these compounds showed cross-resistance to Taxol-resistance A549 cells which do not display the multidrug resistance phenotype. It has recently been shown that eleutherobin demonstrated cross-resistance in an MDR1 expressing cell line derived from human colon carcinoma HCT 116 cells (15).

The compounds SKBII.294, 296 and 298 are derivatives of eleutherobin which lack sugar moiety at the C15 position. Both SKBII.294 and 296 exhibited 54% of the microtubule polymerization activity of eleutherobin and reduced bundle formation in cultured cells. Cytoxicity assays indicated that SKBII.294 was more cytotoxic than to SKBII.296. Compound SKBII.298 with a hydroxymethyl group at the C3 position, was the least active compound in this sub-group. While these studies were being completed, compounds with the same structures as SKBII.294 and 298 were reported to have equal activity (24).

Surprisingly, Compounds SKBII.294 and 296 appear to be considerably less attractive for P-glycoprotein compared to eleutherobin and neo-eleutherobin, suggesting that removal of the sugar or its replacement with an O-acetyl at C15 results in compounds that are essentially not cross-resistant to a cell line that produces high levels of P-glycoprotein. This result is unexpected since one would predict that loss of the sugar moiety would confer increased hydrophobicity and therefore enhance the affinity for P-glycoprotein. Although SKBII.296 demonstrated no cross resistance to SKVBL cells that express high levels of P-glycoprotein, it manifested considerable cross-resistance to the Taxol-resistant cell line not expressing P-glycoprotein. These findings indicate the importance of the glycoside side chain of eleutherobin in modulating drug resistance.

The SKBII.13 derivative differs from the other compounds in that it bears a free hydroxy group rather than an N(1)-methylurocaine acid ester at the C8 position. This compound was found to be biologically inactive. Compared to eleutherobin, its cytotoxicity is greatly reduced and it has forfeited the ability to polymerize microtubules. In certain trials N(1)-methylurocanic acid ester was found to be critical for biological activity of eleutherobin. In trials using a greater number of R group substitutions the role of N(1)-methylurocanic acid ester was found to be important. The R-groupsused in our trials with respect to subsitutions were found to decrease biological activity. (50) After these studies were completed, a similar conclusion was reached in a study of sarcodictyin analogs (24). Clearly, changes in chemical structure can result in differences in biological activity that should be taken into consideration when designing new eleutherobin analogs for clinical studies. However from our trials, it is certain that N(l)-methylurocanic acid ester moiety provides the best activity; other structurally similar moieties may provide the same or still enhance activity.

In 1979, when the mechanism of action of Taxol was first determined, the polymerization of stable microtubules by a small molecule had not been previously described. Recently, in addition to eleutherobin, two other natural products, the epothilones (25) and discondermolide (26,27) have been reported to be cytotoxic to cells and to have very similar mechanism of action to that of Taxol. Although the antitumor activity in humans has been documented for Taxol, it is not known if these newly discovered compounds will be useful cancer chemotherapeutic drugs. The introduction of new drugs into the clinic that may have different pharmacokinetic and pharmocodynamic properties than Taxol and also distinct toxicities and mechanisms of resistance, could prove advantageous for the cancer patient. Structure-activity studies have been reported for the epothilones (28, 29) and taken together with the data reported in this paper for the eleutherobins could lead to the elucidation of a common pharmacophore in these structurally distinct molecules.

References

1. Dustin, P. Microtubules, Ed 2, 482, Berlin: Sprincer-valerg, 1984,

2. Wani, M. C., Taylor, H. L., Wall, M. E., et al., Plant antitumor agents: VI. The isolation and structure of taxol, a novel antileukemic and antitumor agent from *Taxus brevifolia*. *J. Am. Chem. Soc.* 93:2325, 1971, 3. Rao, S., Krauss, N. E., Heerding, J. M., Swindel, C. S., Ringel, I., Orr, G. A. and Horwitz, S. B. 3'-(p-azidobenzamido) taxol photolabels the N-terminal 31 amino-acids of β-tublin. *J. Biol. Chem.*, 269:3131–3134, 1994, 4. Rao, S., Orr, G. A. Chaudhary, A. G., Kingston, D. G. I. and Horwitz, S. B. Characterisation of the Taxol-binding site on the microtubule: 2 -(m-azidobenzoyl) taxol photolabels a peptide (amino acids 217–231) of β-tubulin. *J. Biol. Chem.*, 270:20235–20238, 1995, 5. Schiff, P. B., Fant, J. And Horwitz, S. B. Promotion of microtubule assembly in vitro by taxol. *Nature*(Lond.) 277:665–667, 1979, 6. Schiff, P. B., and Horwitz, S. B. Taxol stabilizes microtubules in mouse fibroblast cells. *Proc. Natl. Acad. Sci.* USA 77:1561–1565, 1980, 7. Jordan, M. A., Toso, R. J., Thrower, D. and Wilson, L. Mechanism of mitotic block and inhibition of cell proliferation by taxol at low concentrations. *Proc. Natl. Acad. Sci.* USA, 90:9552–9556, 1993, 8. Bogdan, C. And Ding, A. Taxol, a microtubule-stabilizing antineoplastic agent, induces expression of tumor and necrosis factor alpha and interleukin-1 in macrophages. *J. Leukoc. Biol.*, 52:119–121, 1992, 9. Ding, A. H., Porteu, F., Sanchez, E. And Nathan, C. F. Shared actions of endtoxin and Taxol on TNF receptors and TNF release. *Science* 248:370–372, 1990, 10. Burkhart, C. A., Berman, J. W., Swindell, C. S. and Horwitz, S. B. Relationship between the structure of Taxol and other taxanes on induction of tumor necrosis factor- α gene expression and cytotoxicity. *Cancer Res.* 54:5779–5782, 1994, 11. Wolfson, M., Huang Yang, C. P. and Horwitz, S. B. Taxol induces tyrosine phosphorylation of SHC and its association with GRB2 in murine RAW 264.7 cells. *Int. J. Cancer,* 70:248–252, 1997, 12. Liu, Y., Bhalla., K., Hill, C. And Priest, D. G. Evidence for involvement of tyrosine phosphorylation in taxol-induced apoptosis in a human ovarian tumor cell line. *Biochemical Pharmacolooy,* 48:1265–1272, 1994, 13. Wang, T. H., Wang, H-S., Ichijo, H., Giannakakou, P., Foster, J. S. Fojo, T. And Wimalasena, J. Microtubule-interfering Agents Active c-Jun N-terminal Kinase/Stress-activated Kinase through both Ras and Apoptosis Signal-regulating Kinase Pathways. *J. Biol. Chem.,* 173–498–4936, 1998, 14. Lindel, T., Jensen, P. R., Fenical, W., Long, B. H. Casazza A. M., Carboni, J. And Fairchild, C. R. Eleutherobin, a new cytoxin that mimics Paclitaxel (Taxol) by stabilizing microtubules. *J. Am. Chem.* 119:3744–8745, 1998, 15. Long, B. H. Carboni, J. M. Wasserman, A. J., Cornell, L. A. Casazza A. M. Jensen P. R., Lindel, T., Fenical, W. and Fairchild C. R. Eleutherobin, a novel cytotoxic agent that induces tublin polymerization, is similar to Paclitaxel (Taxol). *Cancer Res.,* 58:1111–1115, 1998.

16. Nicolau, K. C., Xu, J. Y., Kim, S., Ohshima, T., Hosokawa, S. And Pfefferkorn, J. Synthesis of the tricyclic core of Eleutherobin and Sarcodictyin and total synthesis of Sacrodictyins A. *J. Am. Chem. Soc.,* 119:11353–11354, 1997.

17. Nicolau, KC., van Delft, F., Ohshima, T., Vourloumis, D., Xu, J., Hosokawa, S., Pfefferkorn, J., Kim, S. and Li, T. Total synthesis of the Eleutherobin. *Agnew. Chem. Int. Ed. Engl.,* 37:185–187, 1998, 18. Chen, X. T., Gutteridge C. E., Bhattacharya, S. K. Zhou, B., T. R. R., Hascall, T. and Danishefsky, S. J. A convergent route for the total synthesis of the Eleuthesides. *Agnew Chem. Int. Ed. Engl.,* 110:789–92, 1998, 19. Chen, X. T., Zhou, B., Bhattacharya, S. K. Gutteridge, C. E., Pettus, T. R. R., Hascall and Danishefsky, S. J. The total synthesis of Eleutherobin: A surprise ending. *Agnew Chem. Int. Ed. Enql.,* 110:789–92, 1998, 20. Weisenberg, R. C. Microtubule formation in vitro in solutions containing low calcium concentrations. *Science,* 177:1104–1105, 1972, 21. Kavallaris, M., Kuo, D. Y. S., Burkhart, C. A., Lee Regl, D., Norris, M. D. Haber, M. And Horwitz, S. B. Taxol-resistant epithelial ovarian, tumors are associated with altered expression of specific β-tublin isotypes. *J. Clin. Invest.,* 100:1282–1293, 1997, 22. Bradley, G., Naik, M. And Ling, V. P-glycoprotein expression in multidrug-resistant human ovarian carcinoma cell lines. *Cancer Res.,* 49:2790–2796, 1989, 23. Rowinsky, E. K., Donehower, R. C., Jones, R. J. and Tucker, R. W. Microtubule changes and cytoxicity in leukemic cell lines treated with Taxol. *Cancer Res.,* 48:4093–4100, 1998, 24. Nicolau, K. C., Kim, S., Pfefferkorn, J., Xu, J., Ohshima, T., Hosokawa, S., Vourloumis, D. And Li, T.

Synthesis and Biological Activity of Sacrodictyins. *Anqew. Chem. Int.* Ed. Engl., 37:1418–1421, 1998, 25. Bollag, D. M., McQueney, P. A., Zhu, J., Hensens, O., Koupal, L., Liesch, J., Goetz, M., Lazarides, E. and Woods, C. M. Epothilones, a new class of microtubule-stabilizing agents with a Taxol-like mechanism of action. *Cancer Res.,* 55:2325–2333, 1996, 26. ter Haar, E., Kowalski, R. J., Lin, CM., Longley, RE, Gunasekera, SP., Rosenkranz, HS. and Day, BW. Discoderomolide, a cytotoxic marine agent that stabilizes microtubules more potently than Taxol. *Biochemistry,* 35:243–250, 1996, 27. Hung D. T., Chen. J. And Schreiber, S. L. (+)-Discodermolide binds to microtubules in stoichiometric ratio to tubulin dimers, blocks Taxol binding and results in mitotic arrest. *Chem Biol.,* 3:287–293, 1996, 28. Su, D-S,., Balog. A., Meng, D., Bertinato, P. Danishefsky, S. J., Zheng, Y. H., Chou, T-C., He, L. and Horwitz S. B. Structure-Activity Relationships of the Epothilones and the First In Vivo Comparison with Paclitaxel. *Agnew. Chem. Int. Ed. Engl.,* 36:2093–2096, 1997, 29. Nicolau, K. C., Vourloumis. D., Li, T., Pastor, J., Winssinger, N., He, Y., Nikovic, S., Sarabia, F., Vallberg, H., Roschaogar, F., King, N. P., Finlay, M. R. V., Giannakakou, P., Verdier-Pinard, P. And Hamel, E. Designed Epothilones: Combinatorial Synthesis, Tubulin Assembly Properties, and Cytotoxic Action Against Taxol-Resistant Tumor Cells. Agnew. Chem. Int. Ed. Engl., 36:2097–2102, 1997, 30. D. J. Faulkner *Nat. Prod. Rep.,* 1996, 13, 75, 31. a)W. H. Fenical, P. R. Jensen, T. Lindell (UC) U.S. Pat. No. 5,473,057, 1995 *Chem. Abstr.,* 1996, 102,194297 z];b) T. Lindell, W. H. einical, P. R. Jensen, B. H. Long, A. M. Casazza, J. Carboni, C. R. Fairchild *J. Am. Chem. Soc.,* 1997, 119, 8744, 32. a) M. D'Ambrosio, A. Guerriero, F. Peitra *Helv. Chim. Acta.* 1987, 70, 2019; b) M. D'Ambrosio, A. Guerriero, F. Pietra *Helv. Chim. Acta,* 1988, 71,964, 33. a) O. Kennard, D. G. Watson *Tetrahedron Lett.,* 1968, 2879; b) Y. Lin, C. A. Bowley, D. J. Faulkner *Tetrahedron,* 1993, 49, 7977, 34. D. T. Hung, T. F. Jamison, S. L. Schreiber *Chemistry & Biology,* 1996, 3, 623, 35. R-(–)-α-phellandrene is available from Fluka Chemical Corp., 1001 West Street Paul Avenue., Milwaukee, Wis. 53233, 36. For preparation see: M. A. Keegstra, A. J. A. Klomp, L. Brandsma Synth. Commun., 1990., 20, 3371. For use see: U. Wellmar J. *Heterocycl. Chem.,* 1995, 32, 1159. For 2-iodo-5-magnesium -furan see: W. Gilman, G. F. Wright *J. Am. Chem. Soc.* 1993, 55, 3302. For 2-bromo-5-lithio-thiophene see: M.-J. Shiao, L.-H. Shih, W.-L. Chia, T. -Y. Chau Heterocycles, 1991, 32, 2111, 37. For a Ketene cycloaddition with a cyclohexadiene see the following: a) M. L. Greenlee, *J. Am. Chem. Soc.* 1981, 103, 2425. For a diastereoselective ketene cycloaddition see: A. Kanazawa, P. Delair, M. Pourashraf, A. E. Greene *J. Chem. Soc.* Perkin Trans. I., 1997, 13, 1911, 38. B. M. Trost, M. Preckel, L. M. Leichter *J. Am. Chem. Soc.,* 1975, 97, 2224, 39. Compound 17a (in contrast to the desired 17) undergoes partial lactonization during workup. This lactone can be converted back to 17a. Epimer 17a can be recycled to the synthetic mainstream by oxidation, followed by reduction of the common ketone. These adjustments to the main synthetic stream will be reported in the full paper, 40. For a review of the Nozaki-Kishi reaction see: P. Cintas Synthesis, 1992, 248. See also: M. Eckharkt, R. Bruckner, *Liebigs Ann. Chem.,* 1996, 473, 41. Crystallographic details along with the atom coordinates have been submitted to Cambridge Crystallographic Data Center. No claims, regarding absolute stereochemsitry are based on this data, 42. a)R. J. Ferrier, R. W. Hay, N. Vethaviyasar, *Carbohydr. Res.* 1973,27:5; b)P. J. Garegg, C. Henrichson, T. Norberg, ibid. 1983, 116, 162; c)H. Lonn, ibid. 1985, 139, 105, 115, 43. D. Seebach, N. Meyer *Angew. Chem.* 1976, 88, 484; *Angew. Chem. Int. Ed. Enal.* 1976, 15:438. We also approach the synthesis of the stannyl methyloxy compounds (FIG. 10 step 19 and 20 etc. scheme four and five) by a Schmidt-type (R. R. Schmidt, M. Reichrath, *Angew. Chem.* 1979, 91:497; *Agnew. Chem. Int. Ed. Encl.* 1979, 18:466; R. R. Schmidt, ibid. 1986, 98:213 and 1986, 25:212) alkylation of the anomeric hydroxyl with tributylstannylmethyl iodide. For preparation of the alkylating agent see: a) S. L. Buchwald, R. B. Nielsen, J. C. Dewan, *Organometallics* 1989, 8:1593; b) D. E. Seitz, J. J. Carroll, C. P. Cartaya M., S.-H. Lee, A. Zapata *Synth. Commun.* 1983, 13:129, 44. By conventtions of carbohydrate nomenclature, α and β in the arabinose series correspond to the configurational relationship between C-1 and C-4 of the pyranoside. (For the nomenclature of carbohydrates see: A. D. McNaught *Carbohydr. Res.* 1997, 197. In terms of the structures presented here, α would correspond to the equatorial anomer and β to the axial one; and 45. H. Mawlawi, M. C. Monje, A. Lattes, M. Riviere *J. Heterocycl. Chem.* 1983, 13:129.

46. Nicolaou, K. C., J.-Y. Xu, S. Kim, T. Ohshima, S. Hosokawa, and J. Pfefferkorn. Synthesis of the Tricyclic Core of Eleutherobin and Sarcodictyins and Total Synthesis of Sarcodictyin A. *J. Am. Che. Soc.* 1997, 119, 11353–11354.

47. Nicolaou, K. C., et al., Total Synthesis of Eleutherobin. *Angew. Chem Int. Ed. Enql.* 1997, 36:22.

48. Nicolaou, K. C. Et al., Synthesis and Biological Activity of Sarcodictyins. *Agnew. Chem. Int. Ed.* 1998 37:10.

49. Long, Byron H., et al. Eleutherobin, A Novel Cytotoxic Agent That Induces Tubulin Polymerization Is Similar to Paclitaxel (Taxol). *Cancer Reas.* 1997, 53.

50. Nicolaou, K. C., Solid and Solution Phase Synthesis and Biological Evaluation of Combinatorial Sarcodictyin Libraries. *J. Am. Chem. Soc.* 1998, 120, 10814–10826.

What is claimed is:

1. A process for the preparation of an Eleutherobin analogue of the formula:

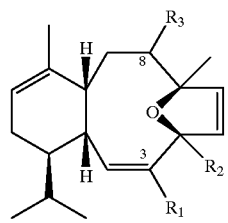

wherein
 $R_1$ is a hydrogen, ester, nitrile, trifolate or $CH_2-R_4$ wherein;
  $R_4$ is a carbohydrate, an alcohol, an amine, an amide, an alkyne,or $C_1-C_9$ linear or branched chain alkyl;
 $R_2$ is a linear or branched alkyl moiety;
 $R_3$ is an ester, an amide, a carbamate, an acetal compound, an ether or a urethane;

position $C_2$ and $C_3$ is cis or trans;

position $C_8$ is α or β, comprising the steps of:

(a) treating a chiral matrix material with a ketene under suitable conditions to form a compound having the structure:

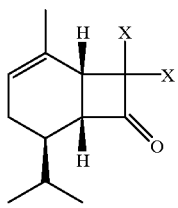

wherein X is a halogen; and (b) dehalogenating the compound in step (a) under suitable conditions to form a compound having the structure:

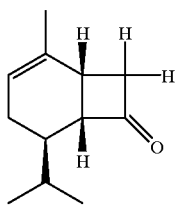

(c) subjecting the compound in step (b) to a Bredereck transformation to form a compound having the structure:

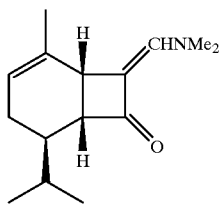

(d) acid catalyzing and fragmenting the compound in step (c) under suitable conditions to form a compound having the structure:

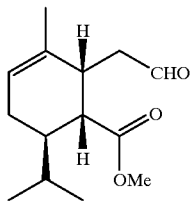

(e) appending a furanoid building block to the compound formed in step (d) under suitable conditions to form a compound having the structure:

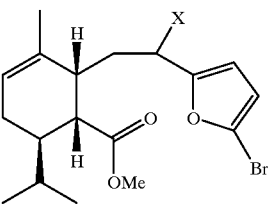

wherein X is α-OH, β-H or α-H, β-OH, (f) protecting the compound formed in step (e) under suitable conditions to form a compound having the structure:

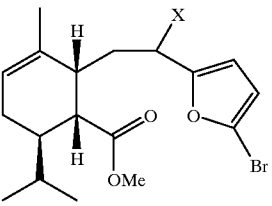

wherein X is α-OTBDPS, β-H or α-H, β-OTBDPS; and (g) expanding the compound in step (f) under suitable conditions to form a compound having the structure:

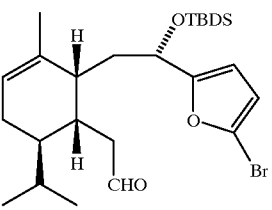

(h) performing a Nozaki-Kishi reaction on the compound in step (g) to form a compound having the structure:

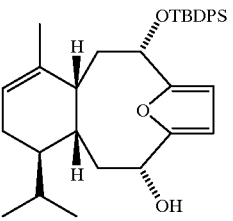

(i) protecting the compound formed in step (h) under suitable conditions to form a compound having the structure:

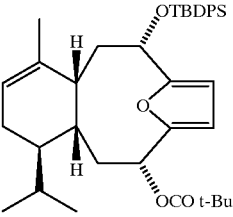

(j) treating the compound in step (i) under conditions suitable to the removal of OTBDPS to form a compound having the structure:

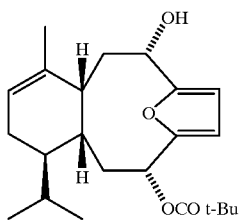

(k) treating the compound in step (j) with dimethyldioxirane under suitable conditions to form a compound having the structure:

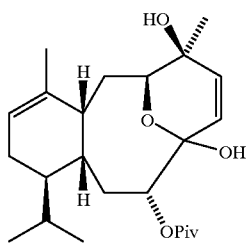

(l) protecting the compound in step (k) under suitable conditions to form a compound having the structure:

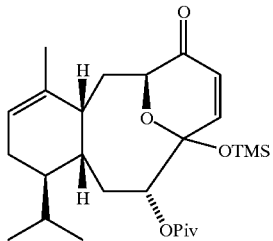

(m) methylating the compound in step (k) or (l) under suitable conditions to form a compound having the structure:

(1)

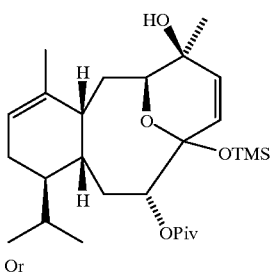

Or

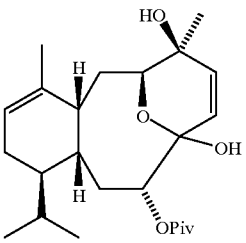

(2)

(n) treating compound (2) in step (m) with acetic anhydride under suitable conditions to form a compound having the structure:

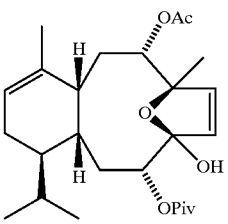

(o) acid catalyzing compound (1) in step (m) under suitable conditions to form a compound having the structure:

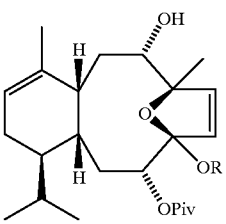

wherein

R is a linear or branched chain alkyl group;

(p) protecting, deprotecting and converting the compound in step (o) under suitable conditions to form a compound having the structure:

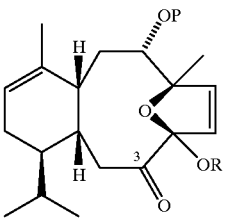

wherein

R is a linear or branched chain alkyl group and P is a protecting group;

(q) treating the compound in step (p) under suitable conditions to form a compound having the structure:

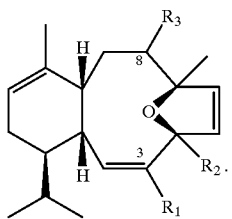

2. The process of claim 1, wherein the chiral matrix material of step (a) is R-(−)-α-phellandrene.

3. The process of claim 1, wherein the furanoid building block comprises a compound having the structure:

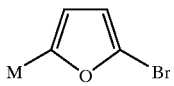

wherein, M is a metal.

4. The process of claim 1, wherein the furanoid building block of step (e) is 2,5-dibromofuran.

5. The process of claim 1, wherein the protecting group is α-OTBDPS, or β-OTBDPS.

6. The process of claim 1, wherein the carbohydrate of step (q) is D-arabinose, L-arabinose or D-galactose.

7. The process of claim 1, wherein the carbohydrate of step (q) is a compound having the structure:

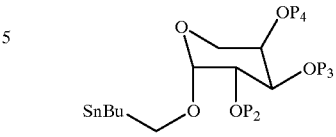

wherein $P_2$, $P_3$, $P_4$, are Ac, SEM. TBS, $C(Me)_2$, or H, with the proviso that $P_2$ is H, SEM, or TBS when $P_3$ and $P_4$ are $C(Me)_2$.

8. A process of claim 1, wherein the carbohydrate of claim 7 is synthesized by converting a compound:

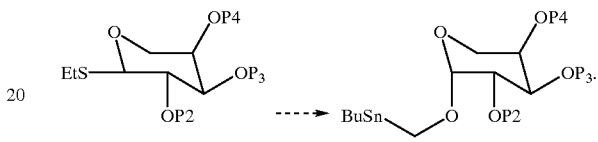

9. The method of claim 1, wherein $R_1$ is H, $R_2$ is OMe, $R_3$ is N(1)-methylurocanic acid ester.

10. A compound produced by the method of claim 6.

* * * * *